(12) United States Patent
Puricelli et al.

(10) Patent No.: US 12,187,663 B2
(45) Date of Patent: Jan. 7, 2025

(54) THYROMIMETICS WITH A BIPHENYLMETHANE SCAFFOLD AND THEIR USE

(71) Applicant: INTERNATIONAL SOCIETY FOR DRUG DEVELOPMENT S.R.L., Milan (IT)

(72) Inventors: Guido Puricelli, Milan (IT); Simona Rapposelli, Lucca (IT); Grazia Chiellini, Rosignano Solvay (IT); Amedeo Columbano, Selargius (IT); Andrea Perra, Quartu Sant'Elena (IT); Massimiliano Runfola, Fordongianus (IT); Sheraz Gul, Hamburg (DE)

(73) Assignee: INTERNATIONAL SOCIETY FOR DRUG DEVELOPMENT S.R.L., Milan (IT)

( * ) Notice: Subject to any disclaimer, the term of this patent is extended or adjusted under 35 U.S.C. 154(b) by 644 days.

(21) Appl. No.: 17/611,188

(22) PCT Filed: Mar. 10, 2020

(86) PCT No.: PCT/EP2020/056388
§ 371 (c)(1),
(2) Date: Nov. 15, 2021

(87) PCT Pub. No.: WO2020/229014
PCT Pub. Date: Nov. 19, 2020

(65) Prior Publication Data
US 2022/0227698 A1    Jul. 21, 2022

(30) Foreign Application Priority Data
May 16, 2019    (IT) .................. 102019000006923

(51) Int. Cl.
*C07C 233/11*    (2006.01)
*A61P 1/16*    (2006.01)
*C07D 209/08*    (2006.01)
*C07D 215/28*    (2006.01)

(52) U.S. Cl.
CPC .............. *C07C 233/11* (2013.01); *A61P 1/16* (2018.01); *C07D 209/08* (2013.01); *C07D 215/28* (2013.01)

(58) Field of Classification Search
CPC ... C07C 233/11; C07D 209/08; C07D 215/28; A61P 1/16
See application file for complete search history.

(56) References Cited

PUBLICATIONS

Search Report and Written Opinion of PCT/EP2020/056388 issued Jul. 1, 2020.
Tancevski I. et al., "The resurgence of thyromimetics as lipid-modifying agents", Current Opinion in Investigational Drugs, vol. 10, No. 9, Sep. 1, 2009, pp. 912-918.

*Primary Examiner* — Timothy R Rozof
(74) *Attorney, Agent, or Firm* — Silvia Salvadori, P.C.; Silvia Salvadori

(57) ABSTRACT

The invention concerns a compound of Formula (I) or a salt thereof, wherein $R_1$ is H, $(C_1\text{-}C_3)$alkyl or $CF_3$; $R_2$ is H, $(C_1\text{-}C_3)$alkyl or $CF_3$; A is $CH_2COOH$, $XCH_2COOCH_2CH_3$, $XCH_2COOH$, $XCH_2CH_2NH_2$, where X is nitrogen or oxygen atom; Ar is an aromatic fragment selected from the group consisting of (Ar1), (Ar2) and (Ar3); where $R_3$ is H, —$CH_3$, —$CH_2CH_3$ or $CH_3CO$—, $R_4$ is H or —$CH_3$, R5 is H or —$CH_3$, and $R_6$ is H or —$CH_3$. The compounds of Formula (I) can be used in the treatment of diseases modulated by thyroid hormone receptor-beta (TRb or TRβ).

16 Claims, 7 Drawing Sheets

29: IS62
30: EP54
31: IS25
32: TG68
33: GM23
34: GM33

| | | colesterolo | glucosio | GOT/AST | GPT/ALT | alfa amilasi | lipasi | bilirubina tot. | trigliceridi |
|---|---|---|---|---|---|---|---|---|---|
| OIL/DMSO | Media | 67.2 | 150.8 | 153.0 | 45.6 | 754.4 | 26.4 | 1.4 | 86.8 |
| | D.S. | 2.5 | 13.5 | 11.1 | 3.7 | 39.1 | 1.9 | 0.2 | 10.4 |
| T3 ig 20 ug | Media | 65.2 | 139.0 | 159.6 | 53.2 | 748.2 | 31.6 | 1.4 | 90.2 |
| | D.S. | 7.1 | 4.4 | 10.6 | 4.1 | 47.0 | 4.6 | 0.3 | 9.3 |
| TG68 ig 50 ug | Media | 68.0 | 128.6 | 140.8 | 46.0 | 760.4 | 22.0 | 1.1 | 70.4 |
| | D.S. | 5.2 | 14.1 | 11.4 | 3.1 | 21.0 | 0.8 | 0.3 | 7.6 |
| TG68 ig 75 ug | Media | 71.4 | 132.2 | 133.0 | 46.2 | 794.2 | 25.0 | 0.9 | 67.0 |
| | D.S. | 6.6 | 7.6 | 8.3 | 1.7 | 46.2 | 2.1 | 0.1 | 12.0 |
| TG68 ig 100 ug | Media | 67.6 | 164.4 | 108.4 | 37.4 | 725.8 | 26.8 | 1.1 | 62.8 |
| | D.S. | 8.1 | 11.6 | 7.0 | 2.5 | 22.3 | 1.2 | 0.2 | 6.1 |
| TG68 ip 75 ug | Media | 71.4 | 131.6 | 134.4 | 38.4 | 775.4 | 29.2 | 1.5 | 74.2 |
| | D.S. | 3.1 | 13.8 | 10.2 | 2.9 | 13.9 | 2.1 | 0.4 | 9.0 |
| IS25 ig 50 ug | Media | 69.5 | 136.0 | 134.5 | 41.3 | 746.3 | 24.8 | 1.3 | 68.3 |
| | D.S. | 9.4 | 6.4 | 6.1 | 2.1 | 33.8 | 1.2 | 0.3 | 9.1 |
| IS25 ig 75 ug | Media | 68.6 | 152.8 | 119.0 | 43.2 | 774.8 | 30.2 | 1.6 | 74.0 |
| | D.S. | 5.6 | 18.1 | 6.4 | 3.3 | 24.9 | 5.0 | 0.2 | 12.8 |
| IS25 ig 100 ug | Media | 70.2 | 166.4 | 102.0 | 42.2 | 755.2 | 28.8 | 1.0 | 67.8 |
| | D.S. | 7.0 | 5.1 | 5.3 | 4.6 | 20.1 | 2.5 | 0.2 | 12.5 |
| IS25 ip 75 ug | Media | 69.6 | 128.8 | 123.8 | 36.0 | 765.2 | 29.8 | 1.1 | 79.6 |
| | D.S. | 1.2 | 9.2 | 10.4 | 1.7 | 26.8 | 3.1 | 0.2 | 9.7 |

Figure 8

THYROMIMETICS WITH A BIPHENYLMETHANE SCAFFOLD AND THEIR USE

This application is a U.S. national stage of PCT/EP2020/056388 filed on 10 Mar. 2020, which claims priority to and the benefit of Italian Patent Application No. 102019000006923 filed on May 16, 2019, the contents of which are incorporated herein by reference in their entireties.

FIELD OF THE INVENTION

The invention concerns novel thyromimetics and their use.

BACKGROUND OF THE INVENTION

Thyroid hormones (THs) are essential regulatory molecules for normal growth and development and for maintaining metabolic homeostasis. (1)

THs play a key role on maintaining the corrected physiological homeostasis such as cardiac function, body weight, metabolism, cholesterol level, bone, muscle and body temperature. Thyroid dysfunction leads to the onset of pathological states, such as hypothyroidism or hyperthyroidism. The activity of THs is mediated by thyroid hormones receptors (TRs). There are two major TR isoforms encoded on separate genes, namely TRα and TRβ, and both TR isoforms bind 3,5,3'-triiodothyronine (T3) and mediate TH-regulated gene expression through interactions with DNA response elements and with several nuclear co-activators and co-repressors.

In the central nervous system (CNS) thyroid hormones exert profound effects in development and maintenance of brain function, influencing various activities such as neuronal and glial cell differentiation, myelination, and neurogenesis (2, 3).

In the liver, THs influence hepatic lipid metabolism through multiple pathways, with insightful effects on energy expenditure (4), fat oxidation (5) and cholesterol metabolism (6). Alteration of cellular TH signaling has been reported to cause liver-associated diseases, such as non-alcoholic fatty liver disease (NAFLD), nonalcoholic steatohepatitis (NASH) and hepatocellular carcinoma (HCC) (7).

Unfortunately, THs cannot be use as pharmacological treatment because of severe adverse side effects which include increased heart rate, cardiac hypertrophy, muscle wasting, and reduced bone density.

Selective modulation of β thyroid hormone receptor (TRβ) has been shown to circumvent many of these undesirable effects, thus suggesting TRβ as potential therapeutic target to regulate lipid metabolism which is essential for treatment and prevention of several chronic diseases such as obesity, diabetes, and cardiovascular diseases (CVDs) without cardiac side effects.

Moreover, in vitro and in vivo studies have provided evidence for the potential utility of the activation of the T3-dependent pathways in metabolic syndrome, non-alcoholic fatty liver disease (NAFLD), and in the treatment of hepatocellular carcinoma (HCC) (7). Thus, a therapeutic strategy based on their use, as single agent or in association, might be effective for the treatment of liver diseases, (i.e. NAFLD, NASH and HCC), that are currently devoid of any effective drug.

Consistently, T3 has been long recognized as a potent hepatomitogen and also such activity seems to be mediated by TR-β1 (8). Although the hepatomitogenic effect of T3 could represent a useful tool in pathological conditions characterized by an impaired regenerative ability (i.e., aged livers), in which a rapid growth stimulation of the liver is required (i.e., human liver transplantation and hepatic resection) [9], its use is hampered by its toxic effects.

Noteworthy, THs take part in several alternative mechanisms of metabolic regulation. Indeed, even if the direct effect on genes transcription involved in metabolism is well established, recently, indirect effects, which involve the activation of alternative cellular pathways, have also emerged (9).

Evidence revealed that free fatty acids generating from stored lipid droplets in the liver require the activation of T3-regulated cellular pathways. And this process seems to be coupled with induction of hepatic autophagy, in which the 5' AMP-activated protein kinase (AMPK) signaling is involved (10).

AMPK is a serine/threonine protein kinase which plays a central role in regulating cellular metabolism and energy balance in mammalian cells (11). Once activated, AMPK triggers several pathways such as glycolysis, fatty acid oxidation, and lipolysis. The overall effects on the lipid metabolism are to stimulate fatty acid oxidation (FAO) and to block cholesterol and triglycerides synthesis (11, 12). Ultimately, it is well known that AMPK/mTOR signaling pathways plays a key role in autophagy process, which is emerging as an important feature to target for the prevention or the treatment of neurodegenerative diseases. On this basis, it is not surprising then AMPK could be itself a target of THs action.

The possible use of THs for treatment of neurodegenerative diseases has also been suggested. In particular, TRβ-selective agonists can enhance oligodendrocytes (OL) differentiation and promote myelination (3, 13). The key role played by TRβ in cell growth, development and in lipid metabolism, corroborate this receptor as a valuable target for the development of new therapies for neurodegenerative diseases such as multiple sclerosis, Alzheimer's disease (AD) and Parkinson's disease (PD).

Unfortunately, nowadays no selective TRβ thyromimetic has entered the clinic, making this class of compounds a target not yet exploited in the clinic.

SUMMARY OF THE INVENTION

Taking into account of all the beneficial effects induced by selective TRβ agonists, new molecules have been developed to be used as single agent or in association, to treat liver diseases (such as NAFLD, NASH, HCC) or neurodegenerative diseases (such as MS, AD, PD) that are currently devoid of any effective drug.

Therefore, the inventors pointed at develop new molecules as selective TRβ modulators which could be helpful for liver-associated diseases, such as non-alcoholic fatty liver disease (NAFLD) and hepatocellular carcinoma (HCC).

It is an object of the invention to provide small molecules capable to induce the following effects: modulation of TRβ,1 induction of hepatomitogenic effects, AMPK activation, lipolitic effects.

The above object has been achieved by a compound of Formula (I):

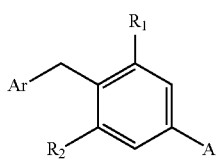

Wherein
R₁ is H, (C₁-C₃)alkyl or CF₃;
R₂ is H, (C₁-C₃)alkyl or CF₃;
A is CH₂COOH, XCH₂COOCH₂CH₃, XCH₂COOH, XCH₂CH₂NH₂, where X is nitrogen or oxygen atom;
Ar is an aromatic fragment selected from the group consisting of

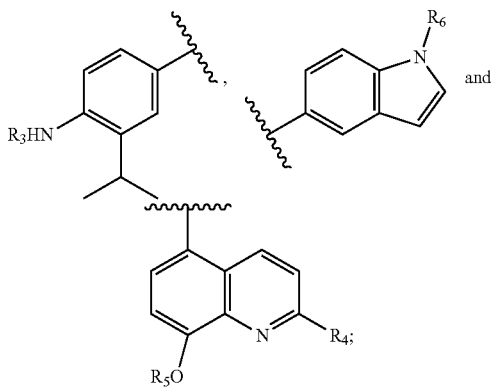

where
R₃ is H, —CH₃, —CH₂CH₃ or CH₃CO—,
R₄ is H or —CH₃,
R₅ is H or —CH₃, and
R₆ is H or —CH₃.

The compounds of Formula (I) demonstrated to be selective thyroid hormone receptor-beta (TRβ) modulators.

In another aspect therefore the invention concerns a compound of formula (I) for use as a medicament, specifically as a selective modulator of thyroid hormone receptor-beta (TRβ).

The inventors then found out TRβ thyromimetic compounds that can be used in the treatment of diseases modulated by thyroid hormone receptor-beta (TRβ).

In a further aspect the invention concerns a compound of formula (I) for use in the treatment of diseases modulated by thyroid hormone receptor-beta (TRβ).

The diseases that can be treated according to the invention are liver diseases (such as non-alcoholic fatty liver disease (NAFLD), non-alcoholic steatohepatitis (NASH) and hepatocellular carcinoma (HCC)), dyslipidemia and neurodegenerative diseases (such as multiple sclerosis, Alzheimer's disease (AD) and Parkinson's disease (PD)).

Advantageously, the compounds of Formula (I) are capable to treat the above listed diseases being selective TRβ thyromimetic compounds.

| % inhibition at 10 μM [compound] | Classification |
|---|---|
| <50 | generally acceptable profile |
| 51-90 | a flag that requires remedial action |
| >91 | major issue (red) that requires significant attention |

Figure 6:
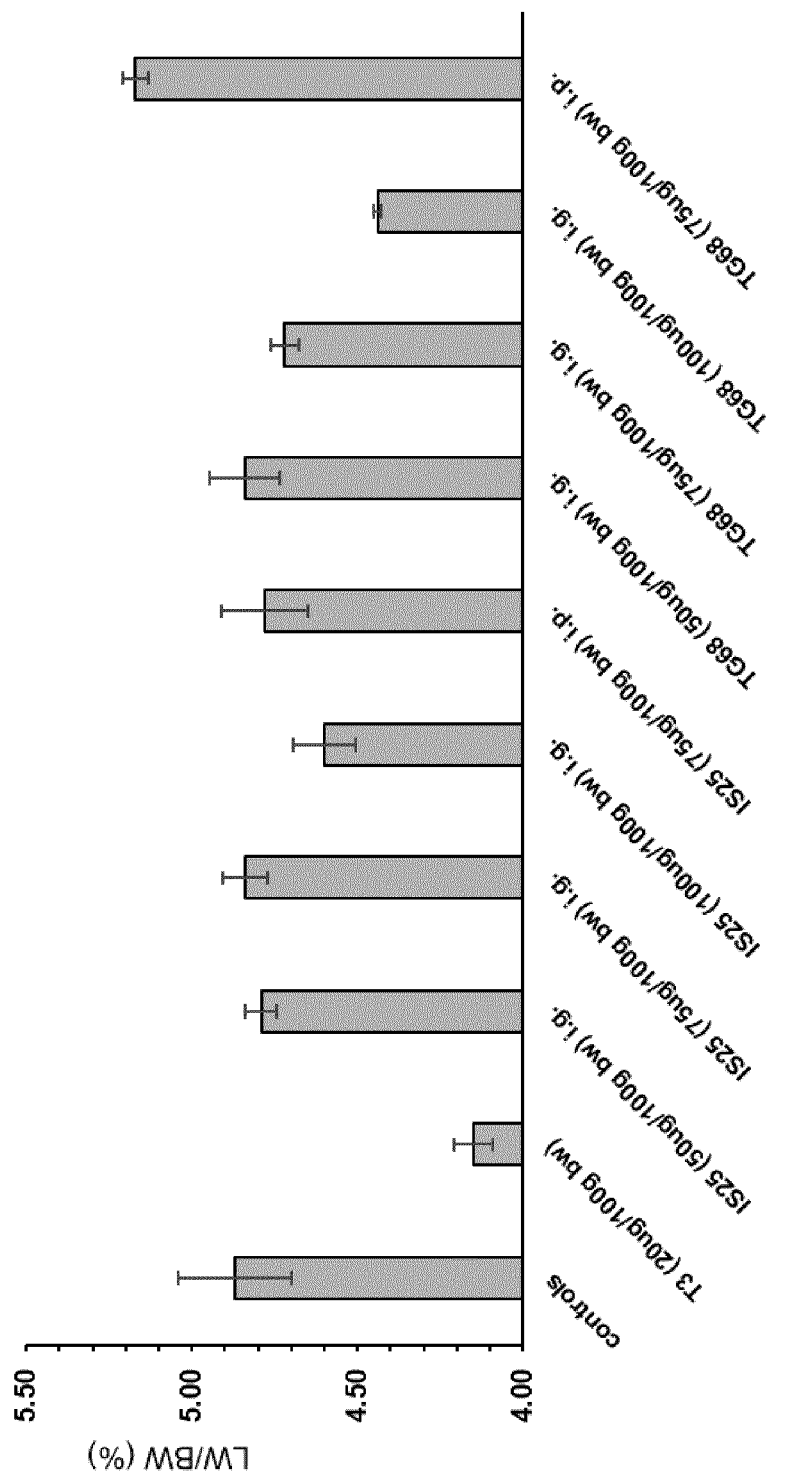

FIG. 6, Effect of T3, IS25 and TG68 on liver/body weight ratio. F344 male rats were treated for 3 days with daily intragastric (IG) injections of IS25 or TG68 (50, 75 and 100 μg/100 g b.w.) or T3 (20 μg/100 g b.w.). A control group received the vehicle (DMSO 5% in corn oil). Additional two groups received daily injections of either IS25 or TG68 at the dose of 75 ug/100 g b.w. intraperitoneally for 3 days. **P<0.01

Figure 7:
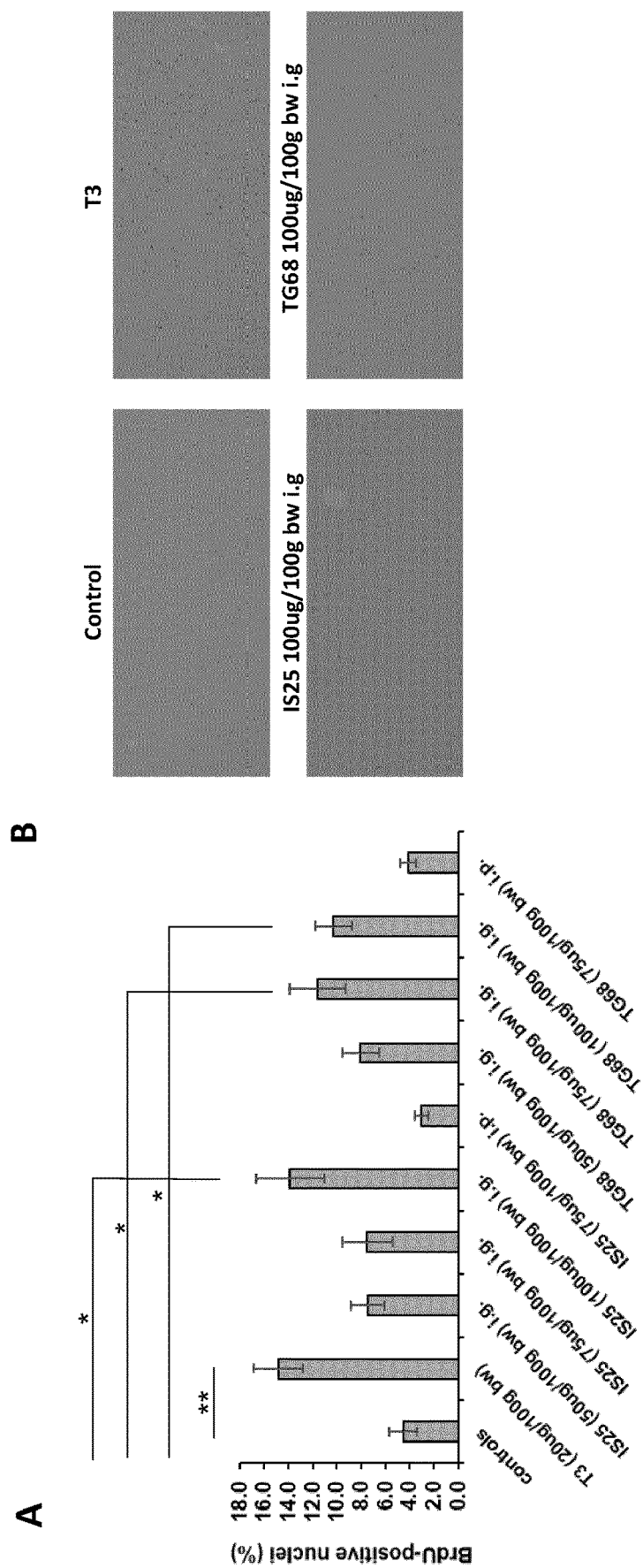

FIG. 7. Effect of T3, IS25 and TG68 on mitotic activity of hepatocytes. For the measurement of hepatocyte proliferation, animals received bromodeoxyuridine (BrdU; 1 g/1 L) in drinking water during the 3-day treatment period with IS25 or TG68 (I.G., 50, 75 and 100 μg/100 g b.w; or i.p. 75 μg/100 g b.w.) or T3 (20 μg/100 g b.w.). A. Labeling Index (L.I.) of hepatocytes from F344 rats subjected to the treatment with test compounds was expressed as number of BrdU-positive hepatocyte nuclei/100 nuclei. Results were expressed as means±S.E. of 3-5 rats per group. At least 3000 hepatocytes per liver were scored. *P<0.05; **P<0.01.

B. Microphotograph illustrating the presence of several BrdU-positive hepatocyte nuclei in the liver of T3, IS25 and TG68 treated rats (sections stained with anti-BrdU antibody and counterstained with hematoxylin).

FIG. 8. Table 1. Serum levels of cholesterol, glucose, hepatic transaminases, alpha-amylase, lipase, bilirubin and triglycerides in rats exposed to the treatment with IS25 or TG68 (i.g., 50, 75 and 100 μg/100 g b.w; or i.p. 75 μg/100 g b.w.) or T3 (20 μg/100 g b.w.) for 3 days.

Figure 9:
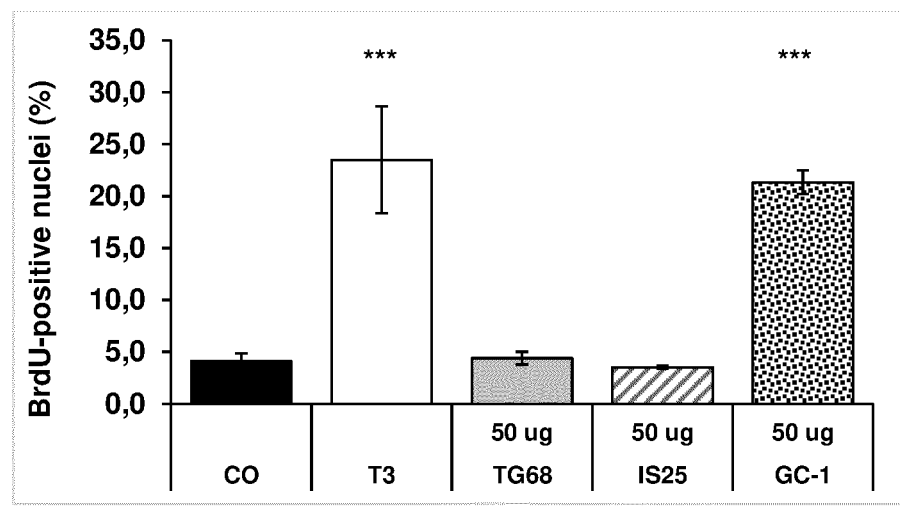

FIG. 9. TG68 or IS25 do not elicit pancreatic acinar cell proliferation. The experiment was performed on untreated rats (CO) or rats treated with T3, GC1, TG68 or IS25 for one week. T3 was administered in the diet (4 mg/kg diet); GC1 (50 μg/kg) was given by gavage once daily; TG68 and IS25 were dissolved in drinking water at a dose of 50 μg/kg. BrdU (1 mg/ml) in drinking water was given all throughout the experimental time. Several BrdU-positive acinar cells are observed in the pancreas of T3 and GC1-treated rats, but not in TG68 and IS25-treated animals; Figure shows the LI of rat pancreatic acinar cells. LI was expressed as number of BrdU-positive acinar cell nuclei/100 nuclei. At least 2000 acinar cells per pancreas were scored. Results are expressed as means±SE of 3 to 5 rats per group. (one way ANOVA). ***Statistically significant from control; P<0.001.

DETAILED DESCRIPTION OF THE INVENTION

The invention relates to a compound of Formula (I) or a salt thereof:

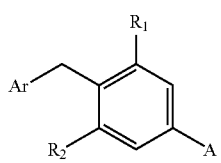

(I)

Wherein
$R_1$ is H, $(C_1-C_3)$alkyl or $CF_3$;
$R_2$ is H, $(C_1-C_3)$alkyl or $CF_3$;
A is $CH_2COOH$, $XCH_2COOCH_2CH_3$, $XCH_2COOH$, $XCH_2CH_2NH_2$, where X is nitrogen or oxygen atom;
Ar is an aromatic fragment selected from the group consisting of

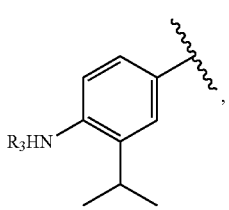

(Ar1)

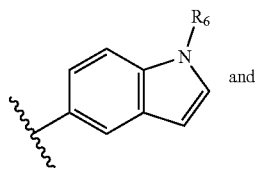

(Ar2)

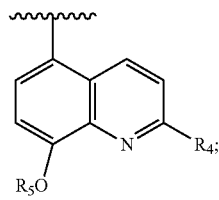

(Ar3)

where
$R_3$ is H, —$CH_3$, —$CH_2CH_3$ or $CH_3CO$—,
$R_4$ is H or —$CH_3$,
$R_5$ is H or —$CH_3$, and
$R_6$ is H or —$CH_3$.
$R_1$ is H, $(C_1-C_3)$alkyl or $CF_3$. Preferably $R_1$ is $(C_1-C_3)$ alkyl, preferably methyl.
$R_2$ is H, $(C_1-C_3)$alkyl or $CF_3$. Preferably $R_2$ is $(C_1-C_3)$ alkyl, preferably methyl.
A is $CH_2COOH$, $XCH_2COOCH_2CH_3$, $XCH_2COOH$, $XCH_2CH_2NH_2$, where X is nitrogen or oxygen atom.
Preferably, A is $XCH_2COOH$, and more preferably X is oxygen.
Ar is selected from the group consisting of Ar1, Ar2 and Ar3.
Preferably Ar è Ar1. More preferably R3 is $CH_3CO$—.
When Ar is Ar2, $R_6$ is preferably $CH_3$.
When Ar is Ar3, $R_4$ is preferably $CH_3$.
The compound of Formula (I) can be used as free base or in a salt form. Preferably, the salt is a salt chosen from hydrochloride, hydrobromides, phosphates, sulphates, hydrogen sulphates, alkylsulphonates, arylsulphonates, acetates, citrates, ossalate, maleates, fumarates, succinates, lactates, and tartrates. A salt can also be formed between a cation and a negatively charged group. Suitable cations include potassium ion, magnesium ion, calcium ion, and an ammonium cation such as tetramethylammonium ion. Examples of some suitable substituted ammonium ions are those derived from: ethylamine, diethylamine, triethylamine, ethanolamine, diethanolamine, piperazine, choline, meglumine, and tromethamine, as well as amino acids, such as lysine and arginine.
Preferably, the compound of Formula (I) is selected from the group consisting of:
2-(4-(4-amino-3-isopropylbenzyl)-3,5-dimethylphenoxy) acetic acid (IS25),
4-(4-(2-aminoethoxy)-2,6-dimethylbenzyl)-N-ethyl-2-isopropylaniline (IS62),
2-(4-(4-amino-3-isopropylbenzyl)-3-methylphenoxy)acetic acid (TR29),
(4-(4-acetamido-3-isopropylbenzyl)-3,5-dimethylphenoxy) acetic acid (TG68),
4-(4-(2-aminoethoxy)-2-(trifluoromethyl)benzyl)-N-ethyl-2-isopropylaniline hydrochloride (EP54),
2-(4-(4-amino-3-isopropylbenzyl)-3-(trifluoromethyl)phenoxy)acetic acid (TR30),
2-(4-(4-acetamido-3-isopropylbenzyl)-3-(trifluoromethyl) phenoxy)acetic acid (TR45), 2-(4-(4-acetamido-3-isopropylbenzyl)phenoxy)acetic acid (GM23),
2-(4-(4-amino-3-isopropylbenzyl)phenoxy)acetic acid (GM33),
2-(4-(4-acetamido-3-isopropylbenzyl)-3-methylphenoxy) acetic acid (GM21),
(4-(4-acetamido-3-isopropylbenzyl)phenyl)glycine (PA8),
ethyl (4-(4-acetamido-3-isopropylbenzyl)phenyl)glycinate (PA6),
$N^1$-(4-((8-methoxy-2-methylquinolin-5-yl)methyl)phenyl) ethane-1,2-diamine (GM10),
2-((4-((8-methoxy-2-methylquinolin-5-yl)methyl)phenyl) amino)acetic acid (GM24),
(4-((1-methyl-1H-indol-5-yl)methyl)phenyl)glycine (TR201), and
2-(4-(4-acetamido-3-isopropylbenzyl)-3-methylphenyl)acetic acid (RM81).

The above compounds are hereinbelow reported with their general structure and have been prepared as disclosed in the experimental part.

-continued

| Compound Name | Structure |
|---|---|
| RM81 | (structure: AcHN-phenyl(iPr)-CH2-phenyl(Me)-CH2-COOH) |

More preferably the compound of Formula (I) is selected from the group consisting of 2-(4-(4-acetamido-3-isopropylbenzyl)-3,5-dimethylphenoxy)acetic acid (TG68), 2-(4-(4-amino-3-isopropylbenzyl)-3,5-dimethylphenoxy)acetic acid (IS25), 2-(4-(4-acetamido-3-isopropylbenzyl)phenoxy)acetic acid (GM23) and 2-(4-(4-amino-3-isopropylbenzyl)phenoxy)acetic acid (GM33)

Still more preferably, the compound of Formula (I) is selected from the group consisting of 2-(4-(4-acetamido-3-isopropylbenzyl)-3,5-dimethylphenoxy)acetic acid (TG68) and 2-(4-(4-amino-3-isopropylbenzyl)-3,5-dimethylphenoxy)acetic acid (IS25).

These latter compounds resulted to be very soluble in water, they were also submitted to preliminary investigation to evaluate whether two novel TRβ agonists, could stimulate hepatocyte proliferation. Therefore, TG68 and IS25 were dissolved in drinking water and the highest dose of them was selected on the basis of the mitogenic activity on rat and mouse liver showed by a similar dose of the analog GC-1 (Sobetirome) [Endocrinology 2006;147(7):3211-8., J Hepatol 2010; 53(4):686-92], that was known as an insoluble compound in water. Advantageously with respect to GC-1, the oral administration resulted then the ideal route of administration for future translational studies.

Furthermore and surprisingly, in a preliminary study shown in the below experimental part the compounds TG68 and IS25 resulted, unlike T3 or GC-1 (chosen as reference drug), were mitogenic only for the liver and not for other tissues, such as the acinar cell compartment of the pancreas The compounds of Formula (I) demonstrated to be selective thyroid hormone receptor-beta (TRβ) modulators.

In another aspect therefore the invention concerns a compound of formula (I) for use as a medicament, specifically as a selective modulator of thyroid hormone receptor-beta (TRβ).

In a further aspect the invention concerns a pharmacological composition comprising the compound of Formula (I) or a pharmaceutically acceptable salt thereof and a carrier. The pharmaceutically acceptable salt of the compound of Formula (I) can be selected from the group consisting of hydrochloride, hydrobromides, phosphates, sulphates, hydrogen sulphates, alkylsulphonates, arylsulphonates, acetates, citrates, ossalate, maleates, fumarates, succinates, lactates, and tartrates. A salt can also be formed between a cation and a negatively charged group. Suitable cations include potassium ion, magnesium ion, calcium ion, and an ammonium cation such as tetramethylammonium ion. Examples of some suitable substituted ammonium ions are those derived from: ethylamine, diethylamine, triethylamine, ethanolamine, diethanolamine, piperazine, choline, meglumine, and tromethamine, as well as amino acids, such as lysine and arginine.

The composition can comprise also pharmaceutically acceptable excipients and can be administered in a pharmaceutical form suitable for the desired administration route. Pharmaceutically acceptable additives can be excipients, ligands, dispersing agents, colorants, humectants, commonly used for the preparation of tablets, capsules, pills, solutions, suspensions, emulsions for oral administration. Injectable solutions are also contemplated for parental administration, comprising subcutaneous, spinal and transdermal administration.

The pharmaceutical composition according to the present invention is preferably for oral and parenteral administration.

The inventors then found out TRβ thyromimetic compounds that can be used in the treatment of diseases modulated by thyroid hormone receptor-beta (TRβ).

In a further aspect the invention concerns a compound of formula (I) for use in the treatment of diseases modulated by thyroid hormone receptor-beta (TRβ).

The diseases that can be treated according to the invention are liver diseases (such as non-alcoholic fatty liver disease (NAFLD), non-alcoholic steatohepatitis (NASH) and hepatocellular carcinoma (HCC)), dyslipidemia and neurodegenerative diseases (such as multiple sclerosis, Alzheimer's disease and Parkinson's disease (PD).

Advantageously, the compounds of Formula (I) are capable to treat the above listed diseases being a selective TRβ thyromimetic compounds.

The invention further provides for a method for selectively modulating the thyroid hormone receptor-beta (TRb). It is also included in the invention a method for treating diseases modulated by thyroid hormone receptor-beta (TRb or TRβ), such as liver diseases (such as non-alcoholic fatty liver disease (NAFLD), non-alcoholic steatohepatitis (NASH) and hepatocellular carcinoma (HCC)), dyslipidemia and neurodegenerative diseases (such as multiple sclerosis, Alzheimer's disease and Parkinson's disease (PD). The method for treating a disease modulated by thyroid hormone receptor-beta (TRb or TRβ) in a subject in need thereof, comprises administering a therapeutically effective amount of a compound or a pharmaceutical composition according to the present invention to the subject, thereby treating or reducing the risk of developing such a disease.

The pharmaceutical compositions according to the present invention can be used alone or in combination with or can comprise one or more further drugs. For example further drugs can be hypocholesterolemic agents such as statins and optionally ion exchange resins or anti-inflammatory agents such as cytokines inhibitor drugs. The invention will be now described with reference to examples.

EXPERIMENTAL PART

Preparation of the Compounds of Formula (I)

Chemistry. General material and methods. Commercial grade anhydrous solvents were used without further drying. Commercially available chemicals were purchased from Sigma-Aldrich or Alfa Aesar and used without further purification. Evaporation was performed in vacuum (rotating evaporator). Anhydrous $Na_2SO_4$ was always used as the drying agent. Flash chromatography was performed on Merck 60 Å high-purity grade silica gel (0.40-63 μm). Reactions were followed by TLC, performed on Merck aluminium silica gel (60 F254) sheets. Spots were viewed under a UV lamp (254 nm) or with the aid 10% phosphomolybdic acid in EtOH. Hydrogenation reactions were performed through HG2000 CLAIND® hydrogen generator. Celite® 545 was used as filter agent.

$^1$H, $^{13}$C and $^{19}$F NMR spectra were obtained using a Bruker Avance 400 spectrometer and were recorder at 400, 101 and 376 MHz, respectively. Chemical shifts are reported in parts per million (ppm) δ values, downfield from the internal reference tetramethylsilane (TMS) and referenced from solvent resonance as the internal standard: deuterochloroform [δ 7.26 ($^1$H spectra), δ 77.16 ($^{13}$C spectra)]; deuterodimethylsulfoxide [δ2.50 ($^1$H spectra), δ 39.52 ($^{13}$C spectra)]; deuteromethanol [δ 3.31 ($^1$H spectra)]. Coupling constants J are reported in hertz (Hz). $^{19}$F and $^{13}$C NMR spectra are $^1$H decoupled. $^{19}$F NMR spectra are unreferenced, corrected from Trifluoroacetic Acid (TFA) as external standard (−76.2 ppm). Signal patterns are indicated as follows: singlet (s), doublet (d), triplet (t), double-doublet (dd), double-triplet (dt), multiplet (m), broad singlet (br s), broad doublet (br d), broad triplet (br t) and broad multiplet (br m).

Abbreviation: DCM=dichloromethane TFA=Trifluoroacetic acid TBTU=N,N,N',N'-Tetramethyl-O-(benzotriazol-1-yl)uronium tetrafluoroborate; DIPEA=N,N-Diisopropylethylamine; DMF=N,N-Dimethylformamide; rt=room temperature Compounds IS25, TR29, TG68, TR30, TR45, GM23, GM33 and GM21 were prepared according to Scheme 1. A Suzuki cross-coupling reaction between compound 1 and the properly substituted phenylboronic acid led to intermediates 2a-d, which were treated with BBr3 at −10° C. to provide the phenolic derivatives 3a-d. Then, O-alkylation reaction of 3a-d with bromoacetic acid led to final compounds TG68, TR45, GM23, GM21. The deacetylation reaction in presence of hydrochloric acid at concentrated grade provided final compounds IS25, TR29, TR30, GM33.

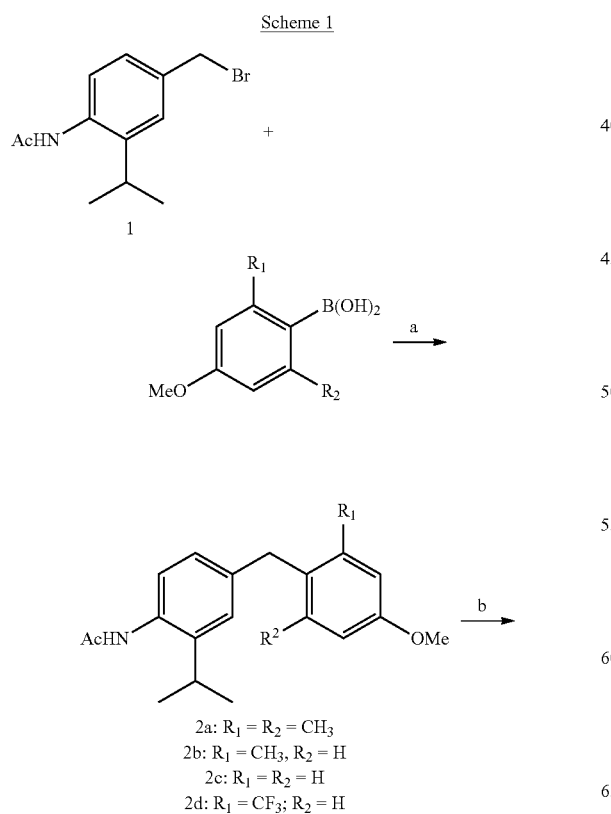

Scheme 1

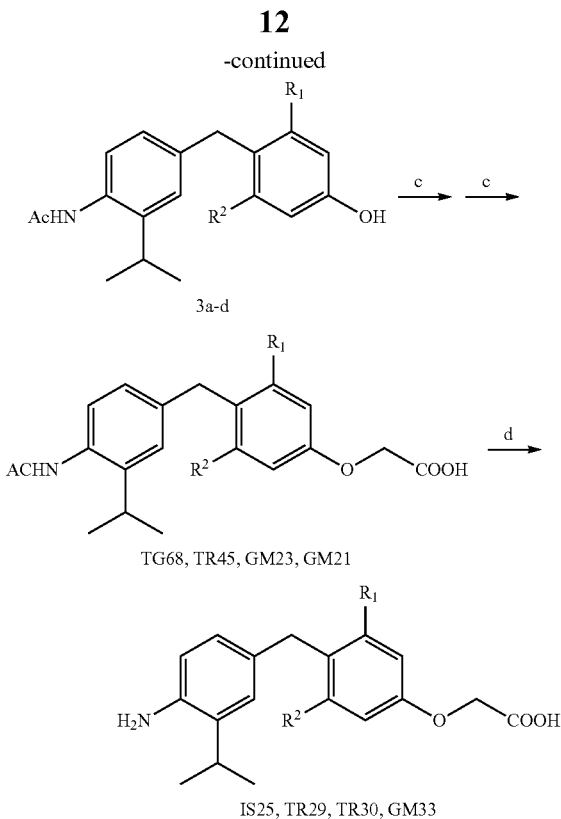

Reagents and conditions:
(a) K2CO3, PdCl2, acetone, H2O, rt, 72 h;
(b) BBr3, DCM, -10° C., 1 h;
(c) BrCH2COOH, DMF, Cs2CO3, rt, 1 h
(d) HCl37%, H2O, 120° C., 12 h Compounds IS62 and EP54 were prepared according to Scheme 2. In particular, phenol 3a,d reacts with bromoacetonitrile yielding compound 4a,d which was then submitted to a reduction with LiAlH4/AlCl3 to afford the compounds IS62 and EP54.

Scheme 2.

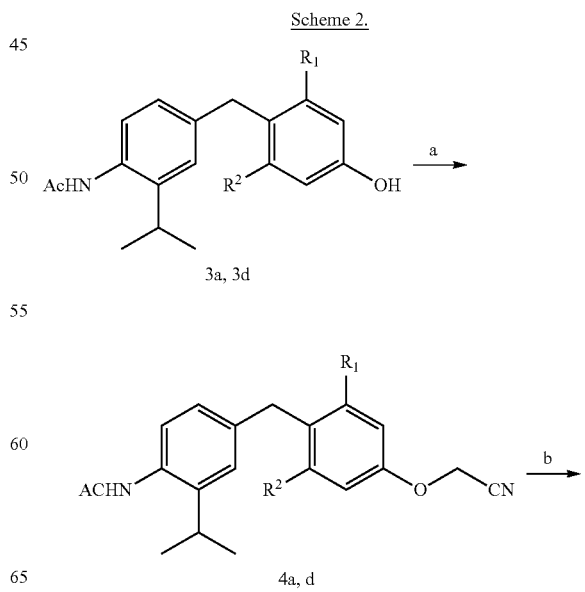

-continued

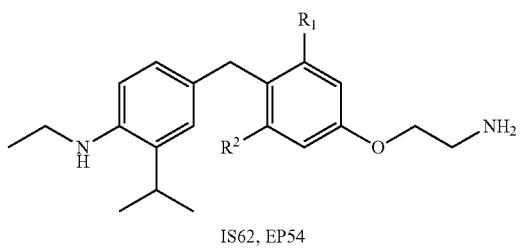

IS62, EP54

Reagents and conditions: a: BrCH₂CN, DMF, Cs₂CO₃, rt., 30 min; b: LiAlH₄, AlCl₃, THF, r.t.-->66° C., 12 h;

The benzyl bromide 1 was obtained following the synthetic procedure reported in Scheme 3. Briefly, a one-pot reaction between aniline 5, acetic anhydride, and bromine was carried out in acetic acid providing the bromobenzene derivative 6 with high yields. Then, formylation reaction of 6 with n-BuLi and DMF at −78° C. led to benzaldehyde-derivative 7, which has undergone reduction with NaBH4 to provide the benzylic alcohol 8. Finally, compound 1 was obtained by bromination of 8, using CBr4 and PPh3.

Scheme 3.

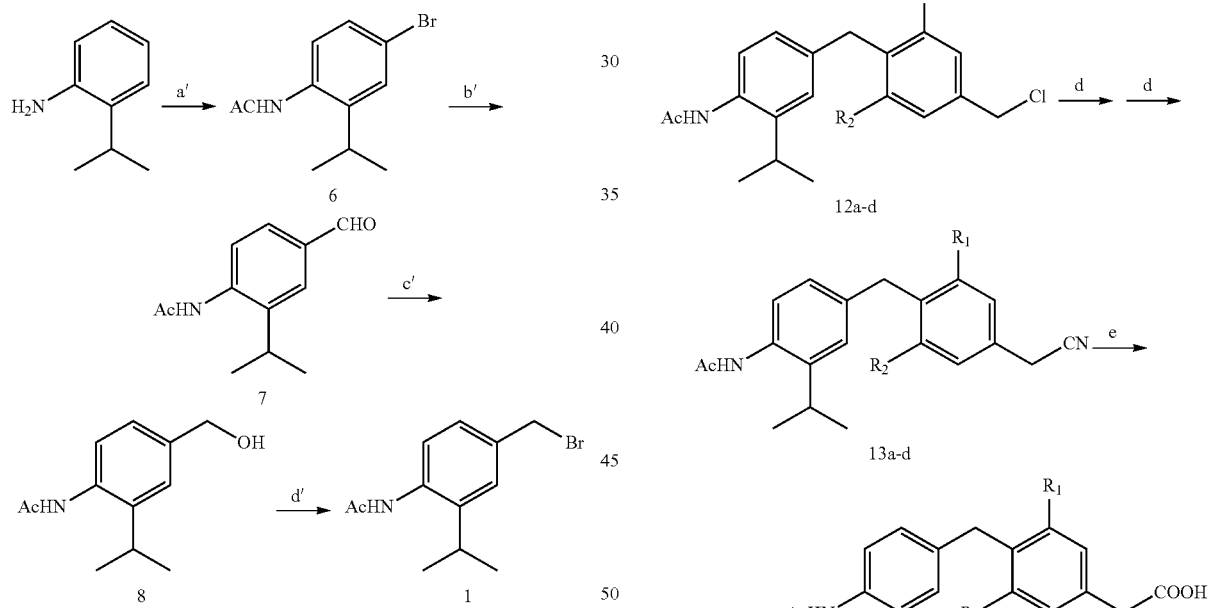

Reagents and conditions:
(a') [1] Ac₂CO, AcOH, 118° C., 1 h; [2]: Br₂, AcOH, 65° C., 30'
(b') n-BuLi, DMF, THF, -78° C. → rt, 3 h;
(c') NaBH₄, MeOH, 0° C. → rt, 12 h;
(d') CBr₄, P(Ph)₃/DCM, 0° C. → rt, 12 h Compound RM81 has been synthesized as reported in Scheme 4. Briefly, the appropriate 4-hydroxymethyl-phenylboronic acid 9a-d reacts with KHF2 to yield the corresponding fluoroboronate salt 10a-d. The subsequent microwave-assisted Suzuki-Myaura cross-coupling reaction with compound 1 led to intermediate 11a-d, which has undergone a chlorination reaction with SOCl2, affording intermediate 12a-d. Then, a microwave-assisted reaction of 13 with NaCN in a mixture of H₂O and AcCN followed by acid hydrolysis with HCl led to RM81.

Scheme 4.

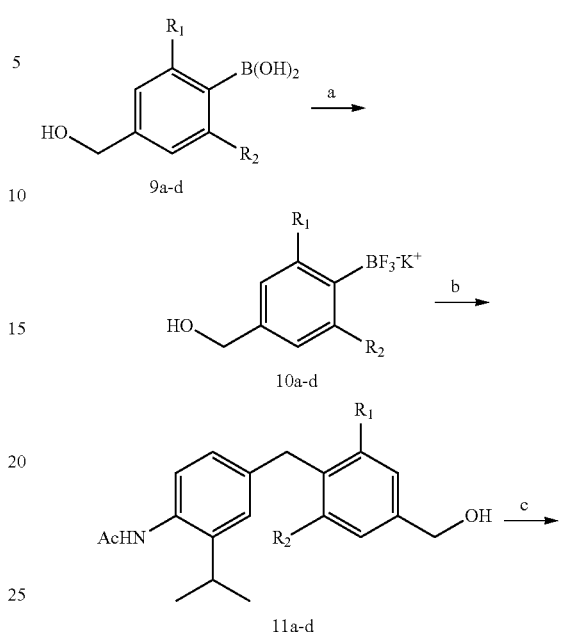

RM81: R1 = Me; R2 = H

Reagents and conditions:
(a) KHF2, MeOH/H2O, rt, 12 h;
(b) mw, 1, Cs2CO3, PdCl2(dppf), H2O/1,4-dioxane, 160° C., 20 min;
(c) SOCl2, CHCl3, 0° C., 90 min;
(d) mw, NaCN, AcCN/H2O, 100° C., 20 min;
(e) HCl 37%, H2O, 120° C., 12 h;

The synthesis of compounds PA8 and PA6 is reported in Scheme 5. Briefly, conversion of derivative 6 with bis (pinacolato)diboron led to compound 14, which has undergone a Suzuki cross coupling reaction with the appropriate 4-nitrobenzylbromide derivative affording derivative 15a-d. Then, selective reduction of 15 with hydrazine in the presence of FeCl3 as catalyst led to amine 16. Finally, N-alkylation of 16 with ethyl bromo acetate or bromoacetic acid provided final products.

afford intermediate 19. The following N-alkylation with bromoacetic acid or with 2-bromoethylamine led to final products GM24 and GM10.

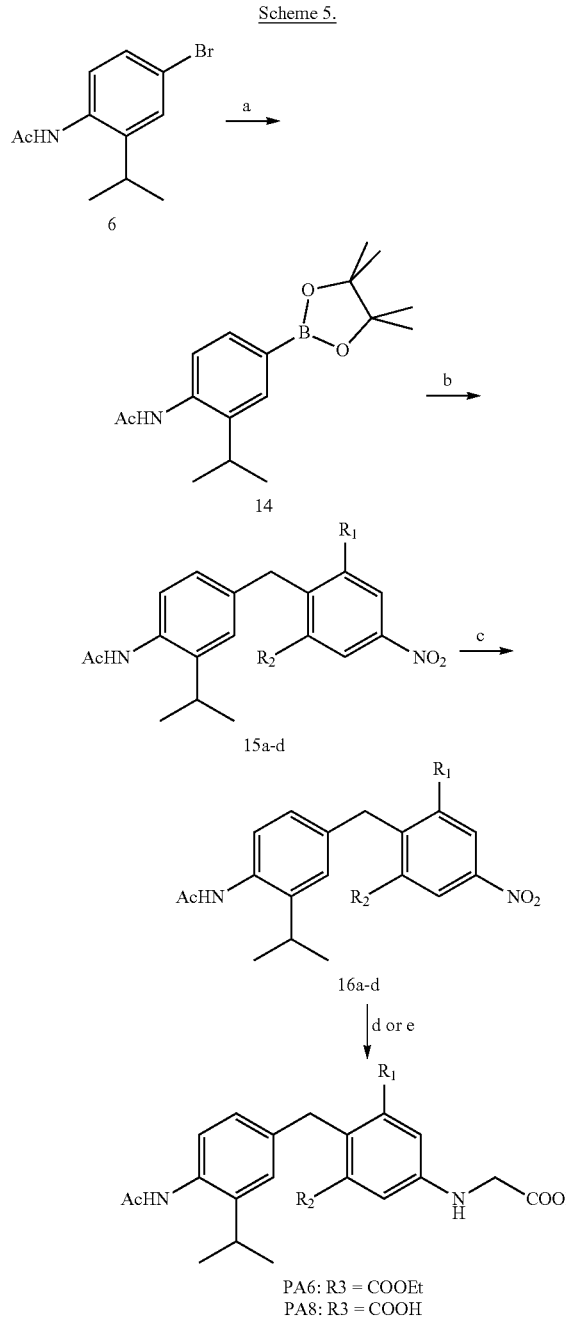

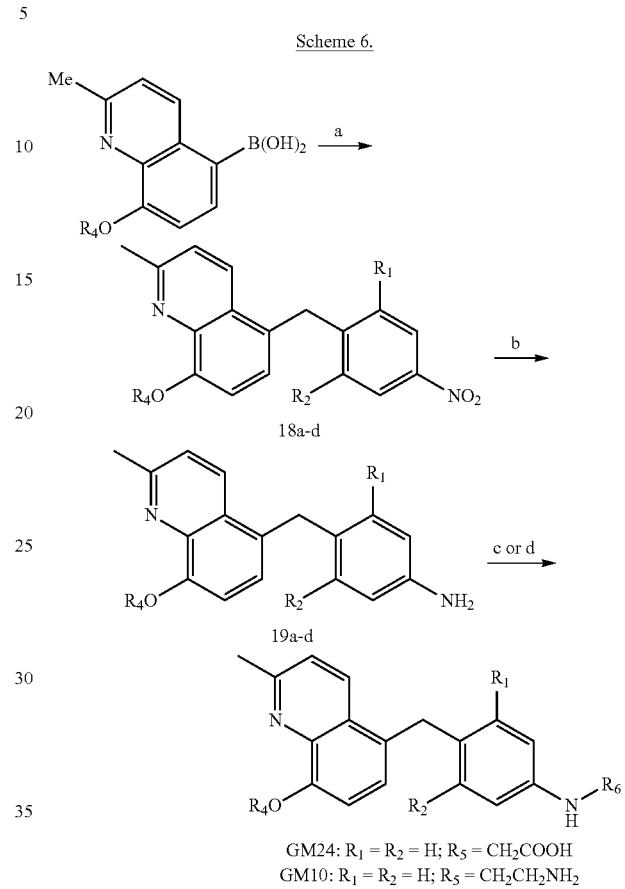

GM24: R₁ = R₂ = H; R₅ = CH₂COOH
GM10: R₁ = R₂ = H; R₅ = CH₂CH₂NH₂

Reagents and conditions:
(a) appropriate 4-nitrobenzylbromide, K₂CO₃, PdCl₂, acetone/H₂O, 72 h, rt;
(b) H₂, Pd/C, MeOH, 12 h;
(c) BrCH₂COOH, DMF, Cs₂CO₃, rt, 1 h;
(d) BrCH₂CH₂NH₂, DMF, CsCO₃, rt, 1 h PA6: R3 = COOEt
PA8: R3 = COOH Reagents and conditions:
(a) B2pin2, PdCl2dppf, KOAc, 1,4-dioxane, 100° C., 4 h,
(b) appropriate 4-nitrobenzylbromide, Na2CO3, PdCl2dppf, 1/2-dimethoxyethane/H2O, 80° C., 12 h
(c) hydrazine, FeCl3, carbon, 12 h, 70° C.;
(d) BrCH2COOEt, EtOH, AcONa, mw 20 min, rt, 1 h
(e) BrCH2COOH, DMF, Cs2CO3, rt, 1 h Finally, Scheme 6 reports the synthetic procedure for the preparation of compounds GM10 and GM24. A Suzuki cross coupling reaction between the appropriate 4-nitrobenzylbromide and boronic acid 17 led to intermediate 18 which has undergone a hydrogenation reduction in presence of Pd/C to Preparation of Intermediates for Synthetizing the Compounds of the Invention General Procedure for the Synthesis of 2a-d Under nitrogen atmosphere, a solution of the appropriate boronic acid (1.25 mmol) in acetone (1.85 mL) and H₂O (0.62 mL) was mixed with K₂CO₃ (431 mg; 3.12 mmol), compound 1 (1.25 mmol), and catalytic PdCl₂. The mixture was stirred at room temperature for 72 h. Then, reaction mixture was concentrated, extracted in DCM, and the organic phase was dried, filtered and evaporated.

N-(2-isopropyl-4-(4-methoxy-2,6-dimethylbenzyl) phenyl)acetamide (2a)

The crude product was purified by flash column chromatography, using a mixture of chloroform and ethyl acetate as eluent (ratio 9:1). 1H -NMR (CDCl₃):δ 1.18 (d, J=6.8 Hz, 6H, CH₃); 2.17 (s, 3H, CH₃CO); 2.21 (s, 6H, CH₃); 2.95-3.02 (m, 1H, CH); 3.79 (s, 3H, OCH₃); 3.95 (s, 2H, CH2); 6.62 (s, 2H, Ar); 6.74 (dd, J=1.6, 8.2 Hz, 1H, Ar);

6.96 (brs, 1H, NH); 6.99 (d, J=1.6 Hz, 1H, Ar); 7.37 (d, J=8.2 Hz, 1H, Ar) ppm. Anal. Calcd for $C_{21}H_{27}NO_2$: C, 70.50%; H, 8.36%; N, 4.30%; Found: C, 77.42%; H, 8.25%, N, 4.43.

N-(2-isopropyl-4-(4-methoxy-2-(trifluoromethyl)benzyl)phenyl)acetamide (2d)

The crude product was obtained following the general procedure. The solvent was 1,4-dioxane and tetrakis(triphenylphosphine)palladium(0) (0.02 mmol) as catalyst Reaction mixture was then added with water and extracted with DCM; organic phase was dried, filtered and concentrated providing a crude that was purified by flash column (eluent: petroleum ether/diethyl acetate, ratio 9:1)

Yield: 22%. 1H-NMR (CDCl3): δ 1.20 (d, J=6.8 Hz, 6H, CH3); 2.20 (s, 3H, CH3); 2.97-3.03 (m, 1H, CH); 3.82 (s, 3H, OCH3); 4.07 (s, 2H, CH2); 6.92-6.96 (m, 2H Ar); 7.06-7.08 (m, 2H Ar); 7.18 (d, J=2.0 Hz, 1H Ar); 7.49 (d, J=8.0 Hz, 1H Ar) ppm. Anal. Calcd for $C_{20}H_{22}F_3NO_2$: C, 65.74%; H, 6.07%; N, 3.83%; Found: C, 65.43%; H, 6.17%, N, 3.71

Synthesis of N-(4-(4-hydroxy-2,6-dimethylbenzyl)-2-isopropylphenyl)acetamide (3a)

A solution of 2 (0.75 mmol) in DCM was cooled to −10° C., and BBr3 (2.37 ml) was added dropwise under nitrogen atmosphere. After 1 h of stirring, the reaction was quenched with H2O and extracted with DCM. Organic phase was then dried over Na2SO4, filtered and evaporated affording compound 3, which was used without further purification Yield: 70% 1H-NMR (CD3OD-d4): □ 1.12 (d, J=6.8 Hz, 6H, CH3); 2.12 (s, 3H, CH3CO); 2.14 (s, 6H, CH3); 3.05-3.08 (m, 1H, CH); 3.95 (s, 2H, CH2); 6.51 (s, 2H, Ar); 6.77 (dd, J=1.8, 8.0 Hz, 1H, Ar); 7.01 (d, J=1.8 Hz, 1H, Ar); 7.03 (d, J=8.0 Hz, 1H, Ar) ppm. Anal. Calcd for $C_{21}H_{25}NO_2$: C, 77.14%; H, 8.09%; N, 4.50%; Found: C, 76.98%; H, 8.26%, N, 4.32%.

Synthesis of N-(4-(4-hydroxy-2-(trifluoromethyl)benzyl)-2-isopropylphenyl) acetamide (3d)

Under nitrogen atmosphere, at −10° C., BBr3 (0.60 ml) was added dropwise to a solution of 2 (0.19 mmol) in DCM; the mixture obtained was stirred for 5' at −10° C. and then, at 0° C. for 1.5 h. After that, reaction was quenched with H2O and extracted with DCM. Organic phase was dried, filtered and evaporated affording final compound. Yield: 88% 1H-NMR (CDCl3): δ 1.19 (d, J=6.8 Hz, 6H, CH3); 2.22 (s, 3H, CH3); 2.97-3.01 (m, 1H, CH); 4.05 (s, 2H, CH2); 6.81 (dd, J=2.4, 8.4 Hz 1H Ar); 6.89 (dd, J=1.6, 8.4 Hz, 1H Ar); 6.94 (d, J=8.4 Hz, 1H Ar); 7.04 (br s, 1H, NH); 7.06 (d, J=1.6 Hz, 1H Ar); 7.11 (d, J=2.4 Hz, 1HAr); 7.41 (d, J=8.4 Hz, 1H Ar) ppm. Anal. Calcd for C19H20F3NO2: C, 64.95%; H, 5.74%; N, 3.99%; Found: C, 64.91%; H, 5.57%, N, 3.94%.

Synthesis of N-(4-(4-(cyanomethoxy)-2,6-dimethylbenzyl)-2-isopropylphenyl)acetamide (4a)

$Cs_2CO_3$ (351 mg; 1.08 mmol) and $BrCH_2CN$ (0.21 mmol) were added simultaneously to a solution of 3 (0.21 mmol) in DMF. The mixture obtained was stirred for 30' at room temperature and then, quenched with water and extracted with DCM. Organic phase was dried over $Na_2SO_4$, filtered and concentrated to obtain final compound. Yield: 73% 1H-NMR (CDCl3): δ 1.18 (d, J=6.8 Hz, 6H, CH3); 2.19 (s, 3H, CH3CO); 2.22 (s, 6H, CH3); 2.95-3.04 (m, 1H, CH); 3.96 (s, 2H, CH2); 4.75 (s, 2H, CH2CN); 6.69 (s, 2H, Ar); 6.72 (d, J=8.4 Hz, 1H, Ar); 6.98 (s, 1H, Ar); 7.39 (d, J=8.4 Hz, 1H, Ar) ppm Anal. Calcd for $C_{22}H_{26}N_2O_2$: C, 75.40%; H, 7.48%; N, 7.99%; Found: C 75.23%; H, 7.52%, N, 7.84%.

Synthesis of N-(4-(4-(cyanomethoxy)-2-(trifluoromethyl)benzyl)-2-isopropylphenyl)acetamide (4d)

A solution of 3 (0.17 mmol) in DMF was treated simultaneously with Cs2CO3 (0.86 mmol) and BrCH2CN (0.17 mmol), and the resulting mixture was stirred for 30' at rt. Then, reaction mixture was quenched with water and extracted with DCM. Organic phase dried over Na2SO4, was filtered and concentrated to obtain final compound. Yield: 29% 1H-NMR (CDCl3): δ 1.18 (d, J=6.4 Hz, 6H, CH3); 2.20 (s, 3H, CH3); 2.96-3.01 (m, 1H, CH); 4.09 (s, 2H, CH2); 4.79 (s, 2H CH2CN); 6.93 (dd, J=1.6, 8.2 Hz, 1H Ar); 7.00 (br s, 1H, NH); 7.05 (dd, J=2.8, 8.8 Hz, 1H Ar); 7.07 (d, J=1.6 Hz, 1H Ar); 7.15 (d, J=8.8 Hz, 1H Ar); 7.27 (d, J=2.8 Hz, 1H Ar); 7.50 (d, J=8.2 Hz, 1H Ar) ppm. Anal. Calcd for C21H21F3N2O2: C, 64.61%; H, 5.42%; N, 7.18%; Found: C 64.81%; H, 5.22%, N, 7.48%.

Synthesis of N-(4-(bromomethyl)-2-isopropylphenyl)acetamide (1)

$CBr_4$ (1.87 mmol) and $P(Ph)_3$ (1.87 mmol) were mixed with a solution of 8 (1.26 mmol) in DCM. Mixture was stirred overnight at rt and then, washed with water and HCl 10%. Organic phase was dried over $Na_2SO_4$, filtered and evaporated; the crude was successively purified by flash column, using ethyl acetate as eluent. Yield: 45%. 1H-NMR (CDCl3): δ 1.25 (d, J=7.2 Hz, 6H, CH3); 2.21 (s, 3H, CH3CO); 2.99-3.03 (m, 1H, CH); 4.48 (s, 2H, CH2Br); 7.04 (brs, 1H, NH); 7.23 (d, J=8.2 Hz, 1H, Ar); 7.29 (s, 1H, Ar); 7.66 (d, J=8.2 Hz, 1H, Ar) ppm. Anal. Calcd for $C_{12}H_{16}BrNO$: C, 53.35%; H, 5.97%; N, 5.18%; Found: C, 53.09%; H, 5.80%; N, 5.39%

Synthesis of N-(4-bromo-2-isopropylphenyl)acetamide (6)

At room temperature, acetic anhydride (1.33 mL; 14.13 mmol) was added to a solution of 2-isopropyl aniline in acetic acid. The mixture was heated at 120° C. and stirred for 1 h under reflux. After cooling reaction mixture to 65° C., a solution of bromine (0.73 mL; 14.13 mmol) in acetic acid was added dropwise, and the mixture obtained stirred for 30'. Then, the mixture was cooled with ice, and unreacted bromine neutralized adding $Na_2S_2O_3$. The suspension obtained was filtered on septum and washed with water, providing a crude mainly composed by compound 6. Yield: 98% 1H-NMR (CDCl3): δ 1.23 (d, J=6.8 Hz, 6H, CH3); 2.20 (s, 3H, CH3CO); 2.95-3.01 (m, 1H, CH); 6.98 (brs, 1H, NH); 7.31 (dd, J=2.0, 8.6 Hz, 1H, Ar); 7.38 (d, J=2.0 Hz, 1H, Ar); 7.54 (d, J=8.6 Hz, 1H, Ar) ppm Anal. Calcd for $C_{11}H_{14}BrNO$: C, 51.58%; H, 5.51%; N, 5.47%; Found: C, 51.23%; H, 5.39%, N, 5.68%.

Synthesis of N-(4-formyl-2-isopropylphenyl)acetamide (7)

At −78° C., under nitrogen atmosphere, n-BuLi (9.79 mmol) was added to a solution of bromobenzene derivative 6 (4.42 mmol) in THF anhydrous. The mixture was stirred for 30' at −78° C.; then, DMF (8.84 mmol) was added, and reaction mixture stirred for 1 h at −78° C. and 1.30 h at room temperature. After this time, reaction mixture was diluted with Et2O and washed with water, HCl 10% and brine. Organic phase was dried, filtered and concentrated. Crude was purified by flash column using a mixture of petroleum ether and ethyl acetate (ratio 7:3) as eluent.

Yield: 39% 1H-NMR (CDCl3): δ1.32 (d, J=6.4 Hz, 6H, CH$_3$); 2.25 (s, 3H, CH$_3$); 2.99-3.04 (m, 1H, CH); 7.23 (brs, 1H, NH); 7.72 (dd, J=1.8, 8.2 Hz, 1H, Ar); 7.83 (d, J=1.8 Hz, 1H, Ar); 8.12-8.23 (m, 1H, Ar); 9.94 (s, 1H, CHO) ppm. Anal. Calcd for C$_{12}$H$_{15}$NO$_2$: C, 70.22%; H, 7.37%; N, 6.82%; Found: C, 70.56%; H, 7.09%, N, 6.61%.

Synthesis of
N-(4-hydroxymethyl-2-isopropylphenyl)acetamide
(8)

At 0° C., a solution of NaBH$_4$ (0.60 mmol) in water was added dropwise to compound 7 (0.60 mmol) previously dissolved in methanol. Reaction mixture was stirred overnight at room temperature; then, mixture was concentrated, and residual aqueous phase extracted in DCM. Organic phase was dried over Na$_2$SO$_4$, filtered and evaporated, affording desired compound 8. Yield: 80% 1H-NMR (CDCl$_3$): δ1.22 (d, J=6.8 Hz, 6H, CH$_3$); 2.20 (s, 3H, CH$_3$); 3.01-3.05 (m, 1H, CH); 4.66 (s, 2H, CH2OH); 7.06 (brs, 1H, NH); 7.18 (d, J=8.0 Hz, 1H, Ar); 7.27 (s,1H, Ar); 7.51 (d, J=8.0 Hz, 1H, Ar) ppm. Anal. Calcd for C12H17NO2: C, 69.54%, H, 8.27%, N, 6.76%; Found: C, 69.80%; H, 8.10%; N, 6.61%.

EXAMPLE 1

Synthesis of 2-(4-(4-acetamido-3-isopropylbenzyl)-3,5-dimethylphenoxy)acetic acid (TG68)

A solution of phenolic derivative 3a-d (0.29 mmol) in DMF was treated with Cs$_2$CO$_3$ (473 mg; 1.45 mmol) and BrCH$_2$COOH (0.29 mmol). The mixture obtained was stirred for 1 h at rt and then, quenched with water. After extraction with DCM, aqueous phase was acidified with HCl 10% and extracted again with DCM. Organic phases were then collected, dried, filtered and concentrated to obtain a crude which was purified by titration in hexane, providing final compound. Yield: 82% (white powder); $^1$H-NMR (CD$_3$OD-d$_4$): δ 1.12 (d, J=6.8 Hz, 6H, CH$_3$); 2.12 (s, 3H, CH$_3$CO); 2.18 (s, 6H, CH$_3$); 3.05-3.08 (m, 1H, CH); 3.98 (s, 2H, CH$_2$); 4.35 (s, 2H, CH$_2$); 6.67 (s, 2H, Ar); 6.76 (dd, J=2.0, 8.0 Hz, 1H, Ar); 7.00-7.08 (m, 2H, Ar) ppm. $^{13}$C-NMR (CD$_3$OD-d4): δ 180.44 (COOH); 172.91 (CH$_3$CO); {158.17, 145.59, 140.71, 139.23, 132.96, 130.42, 128.55, 126.41, 126.32, 115.34} Ar; 68.49 (OCH$_2$); 34.84 (CH$_2$); 29.06 (CH); 24.18 (CHCH$_3$); 23.70 (CH$_3$); 22.81 (CH$_3$CO;); 20.52 (CH$_3$) ppm. Anal. Calcd for C22H27NO4: C, 71.52%; H, 7.37%; N, 3.79%; Found: C, 71.41%; H, 7.42%; N, 3.59%

EXAMPLE 2

Synthesis of 2-(4-(4-amino-3-isopropylbenzyl)-3,5-dimethylphenoxy)acetic acid (IS25)

TG68 (0.29 mmol) and HCl conc. (0.83 mL) were mixed with 4.19 mL of water and refluxed at 120° C. for 12 h. Then, reaction mixture was concentrated, and the crude obtained purified by flash chromatography, eluting with a mixture of hexane-ethyl acetate (ratio 1:1).Yield: 10% (brown oil) $^1$H-NMR (CD$_3$OD-d4): δ 1.15 (d, J=6.8 Hz, 6H, CH$_3$); 2.19 (s, 6H, CH$_3$); 2.92-2.99 (m, 1H, CH); 3.87 (s, 2H, CH2); 4.67 (s, 2H, OCH$_2$); 6.52 (dd, J=1.8, 8.0 Hz, 1H, Ar); 6.61 (d, J=8.0 Hz, 1H, Ar); 6.62 (s, 2H, Ar); 6.79 (d, J=1.8 Hz, 1H, Ar) ppm. 13C NMR (CD3OD-d4): δ171.77, 157.28, 142.51, 139.50, 134.79, 132.24, 131.59, 126.44, 125.77, 117.72, 115.03, 66.02, 52.53, 34.52, 28.32, 23.05, 20.52 ppm. Anal. Calcd for C20H25NO3: C, 73.37%; H, 7.70%; N, 4.28%; Found: C, 73.52%; H, 7.68%; N, 4.19%

EXAMPLE 3

Synthesis of 2-(4-(4-amino-3-isopropylbenzyl)-3-methylphenoxy)acetic acid (TR29)

The synthesis of TR29 was performed following the procedure reported for IS25 and starting from GM21. The reaction mixture was concentrated, and the crude obtained was purified by flash chromatography, eluting with a mixture of hexane-ethyl acetate (ratio 1:1). $^1$H-NMR (CD$_3$OD-d4): δ 1.15 (d, J=6.8 Hz, 6H, CH$_3$); 2.18 (s, 3H, CH3); 2.88-2.94 (m, 1H, CH); 3.87 (s, 2H, CH$_2$); 4.64 (s, 2H, OCH$_2$); 6.70-6.82 (m, 4H, Ar); 7.10-7.13 (m, 2H, Ar) ppm. 13C NMR (CD3OD-d4): δ170.03, 158.23, 141.00, 133.50, 131.51, 131.22, 131.19, 129.71, 127.37, 121.12, 115.43, 64.70, 39.12, 28.40, 23.3, 19.84 ppm. Anal. Calcd for C$_{19}$H$_{23}$NO$_3$: C, 72.82%; H, 7.40%; N, 4.47%; Found: C, 72.52%; H, 7.58%; N, 4.59%

EXAMPLE 4

Synthesis of 2-(4-(4-amino-3-isopropylbenzyl)-3-(trifluoromethyl)phenoxy)acetic acid (TR30)

The synthesis of TR30 was performed following the procedure reported for IS25 and starting from TR45. The crude was purified by chromatography eluting with hexane/AcOEt (3:7). $^1$H-NMR (CD$_3$OD-d4): δ 1.18 (d, J=6.8 Hz, 6H, CH$_3$); 2.86-2.93 (m, 1H, CH); 3.87 (s, 2H, CH$_2$); 4.64 (s, 2H, OCH$_2$); 6.75 (d, J=7.8 Hz, 1H, Ar); 6.79 (s, 2H, Ar); 7.11-7.18 (m, 3H, Ar) ppm. 13C NMR (CD3OD-d4): δ 169.3, 158.23, 141.00, 133.50, 131.51, 131.24, 129.5, 128.3, 127.4, 124.1, 121.5, 118.1, 116.2, 109.7, 64.70, 39.12, 28.40, 23.3 ppm. Anal. Calcd for C19H20F3NO3: C, 62.12%; H, 5.49%; N, 3.81%; Found: C, 63.52%; H, 5.33%; N, 3.75%

EXAMPLE 5

Synthesis of 4-(4-(2-aminoethoxy)-2,6-dimethylbenzyl)-N-ethyl-2-isopropylaniline (IS62)

Under nitrogen atmosphere, AlCl$_3$ (180 mg; 1.35 mmol) was added to a solution of LiAlH$_4$ (1.35 mL; 1.35 mmol) in THF. The mixture was stirred at rt for 5 minutes; then, a solution of derivative 4 (0.15 mmol) in THF was added dropwise, and the mixture refluxed for 12 h. After cooling at 0° C., the mixture was diluted with water, acidified wih HCl 10% and washed with Et$_2$O. Aqueous phase was alkalinized with NaOH 1N and extracted with chloroform; then, organic phase was filtered through celite, washed with brine, dried over Na$_2$SO$_4$ and concentrated. The crude product was then transformed in the corresponding hydrochloride salt. Yield: 15% 1H-NMR (CD$_3$OD-d4): δ 1.23 (d, J=6.8 Hz, 6H, CH3); 1.36 (t, J=7.4 Hz, 3H, CH$_2$); 2.20 (s, 6H, CH$_3$); 3.02-3.06

(m, 1H, CH); 3.36-3.40 (m, 4H, CH$_2$NH$_2$, CH$_2$); 4.07 (s, 2H, CH$_2$); 4.22 (t, J=4.8 Hz, 2H, OCH$_2$); 6.77 (s, 2H, Ar); 6.97 (dd, J=1.4, 8.0 Hz, 1H, Ar); 7.21 (d, J=1.4 Hz, 1H, Ar); 7.27 (d, J=8.0 Hz, 1H, Ar) ppm. 13C NMR (CD$_3$OD-d4): δ 157.89, 144.36, 143.49, 139.71, 130.74, 130.50, 128.61, 127.99, 124.54, 115.19, 65.06, 40.42, 34.67, 28.66, 24.46, 20.43, 20.36, 11.36 ppm. Anal. Calcd for C$_{22}$H$_{33}$ClN$_2$O: C, 70.10%; H, 8.82%; N, 7.43%; Found: C, 70.24%; H, 8.75%; N, 7.56%

EXAMPLE 6

Synthesis of 4-(4-(2-aminoethoxy)-2-(trifluoromethyl)benzyl)-N-ethyl-2-isopropylaniline (EP54)

The crude product was obtained following the same synthetic procedure reported for IS62. The crude was purified by transformation in hydrochloric salt and subsequent re-crystallization in isopropanol/isopropyl ether. Yield: 17%. 1H-NMR (CD$_3$OD-d4): δ 1.27 (d, J=6.4 Hz, 6H, CH3); 1.36 (t, J=7.4 Hz, 3H, CH3); 2.20 (s, 6H, CH3); 3.03-3.04 (m, 1H, CH); 3.38-3.41 (m, 4H, CH2NH2, CH2); 4.19 (s, 2H, CH2); 4.29 (t, J=8.0 Hz, 2H, CH2O); 7.11(dd, J=2.0, 8.4 Hz, 1H, Ar); 7.23 (dd, J=2.4, 8.4 Hz, 1H, Ar); 7.28-7.37 (m, 4H, Ar) ppm. 13C NMR (CD$_3$OD-d4): δ 158.10, 143.52, 135.03, 134.77, 132.28, 131.02, 130.72, 129.55, 128.94, 124.40, 124.19, 119.09, 113.96, 65.76, 40.20, 37.67, 28.74, 24.41, 17.28, 11.42 ppm. Anal. Calcd for C$_{21}$H$_{28}$ClF$_3$N$_2$O: C, 60.50%; H, 6.77%; N, 6.72%; Found: C, 60.51%; H, 6.72%; N, 6.71%

EXAMPLE 7

Synthesis of 2-(4-(4-acetamido-3-isopropylbenzyl)phenoxy)acetic acid (GM23)

The crude product was obtained following the same synthetic procedure reported for TG68. The crude was purified by suspension in hexane .Yield: 64% 1H NMR (CD$_3$OD): δ 1.64 (d, 6H, J=6.8 Hz, CH$_3$); 2.13 (s, 3H, CH3CO); 3.08 (m, 1H, J=6.8 Hz, CH); 3.89 (s, 2H, CH2); 4.61 (s, 2H, CH$_2$COOH); 6.83 (d, 2H, J=8.4 Hz, Ar); 6.98 (dd, 1H, J=2.0, 8.0 Hz, Ar); 7.08 (d, 1H, J=8 Hz, Ar); 7.12 (d, 2H, J=8.4 Hz, Ar); 7.17 (d, 1H, J=2 Hz, Ar) ppm. 13C NMR (CD3OD): δ 172.81 (COON); 172.71 (COCH$_3$); {157.74, 145.62, 142.06, 135.55, 133.10, 130.74, 128.54, 127.48, 127.16, 115.51} Ar; 65.88 (CH$_2$COOH); 41.56 (CH$_2$); 29.02 (CH); 23.59 (CH$_3$); 22.67 (CH$_3$CO) ppm.

EXAMPLE 8

Synthesis of 2-(4-(4-acetamido-3-isopropylbenzyl)-3-methylphenoxy)acetic acid (GM21)

The synthesis was performed following the same procedure reported for compound GM23. The crude was purified by precipitation in a AcOEt/hexane mixture. Yields: 40%. 1H NMR (CD$_3$OD): δ 1.14 (d, 6H, J=6.8 Hz, CH3), 2.13 (s, 3H, CH$_3$CO), 2.93-3.05 (m, 1H, CH), 3.88 (s, 2H, CH$_2$), 4.68 (s, 2H, CH$_2$COOH); 6.85-7.11 (m, 3H, Ar); 7.15-7.35 (m, 3H, Ar) ppm.

EXAMPLE 9

Synthesis of 2-(4-(4-acetamido-3-isopropylbenzyl)-3-(trifluoromethyl)phenoxy)acetic acid (TR45)

The synthesis was performed following the same procedure reported for compound GM21. The crude was purified by precipitation in a AcOEt/hexane mixture. Yields: 25%. 1H NMR (CD$_3$OD): δ 1.18 (d, 6H, J=6.9 Hz, CH$_3$), 2.02 (s, 3H, CH$_3$CO), 2.19 (s, 3H, CH$_3$), 3.08 (m, 1H, J=6.8 Hz, CH), 3.91 (s, 2H, CH$_2$), 4.70 (s, 2H, CH$_2$COOH); 6.72-6.78 (m, 2H, Ar); 6.89 (dd, 1H, J=2.0, 8.0 Hz, Ar); 7.03 (d, 1H, J=8.4 Hz Ar), 7.07 (d, 1H, J=8.0 Hz, Ar); 7.10 (s, 1H, Ar) ppm.

EXAMPLE 10

Synthesis of 2-(4-(4-amino-3-isopropylbenzyl)phenoxy)acetic acid (GM33)

The crude product was obtained following the same synthetic procedure reported for TG68. The crude was purified in hexane. Yield: 96%. 1H NMR (CD$_3$OD): δ 1.26 (d, 6H, J=6.8 Hz, CH3); (m, 1H, J=6.8 Hz, CH); 3.94 (s, 2H, CH$_2$); 4.62 (s, 2H, CH2COOH); 6.86 (d, 2H, J=8.4 Hz, Ar); 7.12 (d, 3H, J=8.8 Hz, Ar); 7.25 (d, 1H, J=2.0, 8.0 Hz, Ar); 7.34 (s, 1H, Ar); 7.91 (s, 1H, COOH) ppm. 13C NMR (CD$_3$OD): δ 171.44 (COOH); {157.82, 144.57, 143.37, 135.01, 130.83, 128.63, 128.60, 124.20, 115.67} Ar; 66.03 (CH$_2$COOH); 41.29 (CH$_2$); 28.64 (CH); 23.79 (CH$_3$) ppm.

EXAMPLE 11

Synthesis of 2-((4-((8-methoxy-2-methylquinolin-5-yl)methyl)phenyl)amino)acetic acid (GM24)

Cs$_2$CO$_3$ (0.59 mmol) and bromoacetic acid (0.12 mmol) are added simultaneously to a solution of amine 19 (0.12 mmol) in DMF and the reaction is left at room temperature and monitored by TLC (CHCl$_3$/iPrOH 9:1). After 24 h the reaction is extracted with dichloromethane and the organic phase is dried, filtered and evaporated. The crude product was purified by flash chromatography eluting with DCM/isopropanol.

EXAMPLE 12

Synthesis of N1-(4-((8-methoxy-2-methylquinolin-5-yl)methyl)phenyl)ethane-1,2-diamine (GM10)

To a solution of amine 19 (0.10 mmol) in H$_2$O was added bromoethylamine (0.05 mmol) the reaction was stirred at 95° C. for 12 h. Then, the reaction was allowed to r.t and diluted with AcOEt. The aqueous phase is then alkalinized and re-extracted with dichloromethane. The organic phase was then anhydrified, filtered and evaporated. The crude product was purified by flash chromatography eluting with DCM/isopropanol.

EXAMPLE 13

Synthesis of 2-(4-(4-acetamido-3-isopropylbenzyl)-3-methylphenyl)acetic acid (RM81)

A solution of derivative 13 (92 mg, 0.287 mmol) in concentrated sulfuric acid and distilled water (50% v/v) is refluxed for 30 minutes. After that time, distilled water is added until formation of a precipitate which is filtered and purified by crystallization from isopropanol/diisopropyl-ether. $^1$H-NMR (MeOD): δ 1.15 (d, J=6.8 Hz, 6H, CH$_3$), 2.13 (s, 3H, CH$_3$), 2.21 (s, 3H, CH$_3$), 3.08 (m, J=6.8 Hz, 1H, CH), 3.54 (s, 2H, CH$_2$), 6.91 (dd, J=2.0, 8.0 Hz, 1H, Ar), 7.04-7.09 (m, 4H, Ar), 7.13 (d, J=2.0 Hz, 1H, Ar) ppm.

EXAMPLE 14

Synthesis of ethyl 2-((4-(4-acetamido-3-isopropylbenzyl)phenyl)amino)acetate (PA6)

Ethyl bromoacetate (0.355 mmol) and AcONa (0.355 mmol) are added to a solution of aniline 16a (0.355 mmol) in EtOH. The resulting mixture is placed to react in a microwave reactor at 118° C. for 15 minutes. After this period, the reaction is cooled and diluted with water. The precipitation of a solid is observed which is filtered and dried to supply the final product, which was subsequently purified by chromatography eluting with a mixture $CHCl_3$/MeOH (99:1). Yields: 32%. 1H NMR (MeOD): δ 1.18 (d, 6H, J=7 Hz, CH3); 1.25-1.31 (m, 3H, CH3); 2.14 (s, 3H, CH3CO); 3.10 (m, 1H, J=7 Hz, CH); 3.85 (s, 2H, CH2); 4.17-4.23 (m, 2H,CH2); 6.54 (d, 2H, J=8.8 Hz, Ar); 6.98 (dd, 1H, J=2.0 Hz, J=8.2 Hz, Ar); 7.04 (d, 2H, J=8.8 Hz, Ar); 7.08 (d, 1H, J=8.2 Hz, Ar); 7.17 (s, 1H, Ar) ppm. 13C NMR (MeOD): δ 14.49; 22.78; 23.72; 29.14; 42.75; 54.45; 62.13; 113.46, 127.22, 127.57, 128.58, 130.57, 131.94, 133.06, 142.57, 145.65, 147.61; 172.99; 173.06 ppm.

EXAMPLE 15

Synthesis of 2-((4-(4-acetamido-3-isopropylbenzyl)phenyl)amino)acetic acid (PA8)

A solution of PA6 (0.052 mmol) in EtOH (q.b.) was added with 0.01 mL NaOH 10%. The mixture thus obtained is left under stirring at reflux at 78° C. for 30 minutes and, after this period, HCl is added up to acid pH. The reaction mixture is extracted with DCM. The organic layers evaporated gave the final product, which was purified by precipitation in AcOEt/Hexane. Yields 67%. 1H NMR (MeOD): δ 1.16 (d, 3H, J=6.8 Hz, CH3); 2.12 (s, 3H, CH3CO); 3.04-3-11 (m, 1H, CH); 3.85 (s, 2H, CH2); 4.15 (s, 2H, CH2); 6.51 (d, 1H, J=8.4 Hz, Ar); 6.57 (d, 1H, J=8.4 Hz, Ar); 6.96-6.99 (m, 2H, Ar); 7.01-7.11 (m, 2H, Ar); 7.16 (s, 1H, Ar) ppm. 13C NMR (MeOD): δ 22.80; 23.68; 29.13; 41.87; 47.27; 121.63, 123.15, 124.08, 127.45, 127.67, 128.89, 131.60, 131.83, 131.95, 140.90; 146.01; 173 ppm.

Evaluation of the Compounds of Formula (I)

The activity of the compounds against TRalpha and TRbeta were assayed utilizing methods known in the art and/or methods presented therein.

Methods

Cells Culture and Treatment

Human hepatocellular carcinoma cells (HepG2), obtained from American Type Culture Collection (Manassas, Va., USA), were cultured in low-glucose (LG) Dulbecco's modified Eagle's medium (DMEM) (5.5 nM, Invitrogen, Carlsbad, Calif., USA) or high-glucose (HG) DMEM (30 nM) supplemented with 10% fetal bovine serum (FBS) and 10 mg/ml penicillin/streptomycin in an atmosphere of 5% $CO_2$ at 37° C. These cells were then treated with tested compounds at various concentrations for 24 h. After treatments, cells were lysed in a buffer containing 20 mM Tris-HCl (pH 7.5), 0.9% NaCl, 0.2% Triton X-100, and 1% of the protease inhibitor cocktail (Sigma-Aldrich, Milan, Italy) and then stored at −80° C. for further western blot analysis. All the analyses were conducted on cells between the third and the sixth passage.

Western Blotting Analysis

Proteins (20-30 μg) were separated on CriterionTGX™ gel (4-20%) and transferred on Immuno-PVDF membrane (Biorad, Milan, Italy) for 1 h. Blots were incubated with the primary antibody at 4° C. overnight. All the polyclonal antibodies for the protein of interest were purchased from Santa Cruz Biotechnology, Inc., Dallas, TX, USA. Then, blots were washed 3 times for 10 minutes with 1×TBS, 0.1% Tween® 20 and incubated for 1 h with secondary antibody (peroxidase-coupled anti rabbit in 1×TBS, 0.1% Tween®20). After washing 3 times for 10 minutes, the reactive signals were revealed by enhanced ECL Western Blotting analysis system (Amersham). Band densitometric analysis was performed using Image Lab Software (Biorad, Milan, Italy).

Determination of Total Lipid Accumulation by Oil Red O Staining

Total lipid accumulation was evaluated according to the method previously described by Liu et al. [20]. Cells were seeded at a density of $3.5 \times 10^4$ cells/well in 24-well plates and treated for 24 h with compound IS25, TG68, or T3 at two different doses, 1 and 10 μM. Cloroquine (25 μM) and Isoproterenol (10 μM) were used as positive controls. Subsequently, after collecting the growth media to be used to perform glycerol level measurements (as detailed below), cells were rinsed twice with PBS and fixed in 4% paraformaldehyde in PBS for 30 min. Then, cells were stained with Oil Red O working solution for 1 h at room temperature and subsequently rinsed with water.

The Oil Red O stock solution was prepared by dissolving 0.35 g of Oil Red O (Sigma Aldrich, Milan, Italy) in 100 mL of isopropanol by gentle heating and then cooled and filtered through a 0.45 μm filter. The working solution was prepared by diluting three parts of the stock solution in two parts of MilliQ water (stock solution:MilliQ water; 3:2 v/v). The cell images were captured with a Leitz Fluovert FU (Leica Microsystems, Wetzlar, Germany) microscope. Lipids appeared red. For quantitative analysis of cellular lipids, 1 mL isopropanol was added to each well of the stained culture plate. The extracted dye was immediately removed by gentle pipetting and its absorbance was measured at 510 nm.

Determination of Glycerol Release

Samples of the media collected from HepG2 cells used to test lipid accumulation by Oil Red O staining (as detailed above), were assayed for glycerol levels using the Glycerol Assay Kit (Cell Based-ab133130-Abcam).

Cell Viability Assay MTT Assay

HepG2 cells were seeded in a 96-well plate (Corning, USA) at a density of $1.0 \times 10^4$ cells/well with DMEM (200 μl/well), and then incubated for 24 h according to routine procedure. After being treated with test compounds (1-10 μM) and incubated for 24 h (8 wells for each sample), 20 μL/well MTT (5 g/L) was added to each well. The medium was then removed after 4 h incubation and 100 μL/well sodium dodecyl sulfate (SDS)-HCl solution was added to dissolve the reduced formazan product after incubation for 16 h at 37° C. Finally, the plate was read at 570 nm, using a micro-plate reader (Bio-Rad 680, USA).

In Vitro ADME-TOX Profiling

Cytotoxicity Assay

Test compounds (20 nL of 10 mM top concentration in 100% v/v DMSO), positive control (PC; Valinomycin with final concentration of 10 µM and 0.1% v/v DMSO) and NC (final 0.1% v/v DMSO) were added in an empty polystyrene 384-well cell culture microtiter plate using the Echo 550 Liquid Handler and stored at room temperature before cell's seeding. U2OS, hTERT, MCF-7, and HEK293 cells were grown on surface-modified T175 cell culture flasks in Dulbecco's Modified Eagle Medium (DMEM) with 10% fetal bovine serum (FBS), 5% of L-Glutamic acid, 5% streptomycin, and 5% penicillin G. At about 80% of confluency, cells were washed, trypsinized, resuspended, and counted in DMEM before seeding (in triplicate) into white 384-well microtiter plates containing compounds (20 µL) at 4000 cells/well and incubated at 37° C. in the presence of 5% CO2. At 24 h and 48 h post-treatment, 20 µL/well of CTG detection mix were added, and plates were read using an EnVision Multilabel 2103 Reader after a 10-min incubation in the dark. The raw data were normalized to percentage of cell growth by using the corresponding NC containing only 0.1% v/v DMSO. The luminescence signal of each sample (S) was converted into percentage of cell growth compared with the average signal of NC. The following formula was used: % effect=(S−PC)/NC×100.

Cytochrome (CYP) P450 Inhibition Assay

These assays (at least in duplicate) make use of microsomal preparations of CYP450 (2C9, 2C19, 2D6, and 3A4) from baculovirus-infected insect cells (Corning Inc.) and cytochrome c reductase (and cytochrome b5 for CYP450 3A4). For detection of CYP450 activity, the luminescence-based P450-Glo (Promega Corp.) assay system was used that contained a luminogenic CYP450 substrate, lyophilized luciferin detection reagent, and reconstitution buffer. The substrates were luciferin derivatives of CYP450-specific substrates that produce (4S)-4,5-dihydro-2-(6-hydroxybenzothiazolyl)-4-thiazolecarboxylic acid (D-luciferin) after cleavage by CYP450 (CYP450 3A4, luciferin-IPA; CYP450 2C19, luciferin-H EGE; CYP450 2C9, luciferin-H; CYP450 2D6, luciferin-ME EGE). CYP450 reactions were initiated by addition of the NADPH regeneration system to the enzyme-substrate mixture with the luciferin detection reagent stopping the reaction and the D-luciferin being converted to oxyluciferin under production of light being proportional to the CYP450 activity. Compounds were added into an empty 384-well plate (10 nL/well in 0.1% v/v DMSO) using the Echo 550 Liquid Handler followed by addition of 5 µL/well of CYP450/substrate mixture and incubation for 30 min at 37° C., after which the reaction was initiated by addition of 5 µL/well NADPH regeneration system. After a further 30-min incubation at 37° C., the CYP450 reaction was stopped, and the luciferase reaction was simultaneously initiated by addition of 10 µL/well of luciferin detection reagent, followed by an additional 30-min incubation at 37° C. The luminescence signal was detected using an EnVision Multilabel 2103 Reader.

hERG Cardiotoxicity Assay

The Predictor hERG fluorescence polarization assay (Thermo) was used to test compounds for potential cardiotoxicity (in triplicate). To each well of an assay plate, 100 nL of the test/control compound was added followed by addition of 5 µL homogenized membrane solution (undiluted) and 5 µL of tracer (1 nM final concentration in assay). The plates were incubated for 2 h at 25° C. in a humidity controlled incubator, and the fluorescence polarization was measured using an EnVision Multilabel 2103 Reader. The NCs (0% inhibition) and positive controls with E-4031, a blocker of hERG-type potassium channels (yielding 100% inhibition), were used to normalize the raw data.

HDAC Assay

Inhibition of HDAC enzymes (in triplicate) was determined using the homogeneous, single-addition, bioluminogenic HDAC-Glo I/II assay (Promega Corp.). The kit contains a proluminogenic substrate with an acetylated lysine peptide sequence derived from histone 4 conjugated to aminoluciferin. HDAC-mediated deacetylation of the lysine residue facilitates luminogenic substrate susceptibility to specific proteolytic cleavage by the enzyme in the developer reagent. The aminoluciferin product of that cleavage acts as a substrate for luciferase, and the amount of light produced in this reaction is proportional to HDAC enzyme activity. Human recombinant HDAC enzymes were purchased from BPS Bioscience (San Diego, CA), and standard inhibitor trichostatin A (Sigma-Aldrich) was dissolved to a yield stock solution in 100% v/v DMSO and stored at −20° C. Plate handling was performed using an Echo 550 Liquid Handler and luminescence measurements taken using a 2300 EnSpire Multilabel reader. The compounds/positive control (trichostatin A with final concentration of 10 µM and 0.1% v/v DMSO) and high control (final 0.1% v/v DMSO) were added into the 384-well plates (10 nL/well; 0.1% v/v DMSO) using the Echo 550 Liquid Handler. The HDAC-Glo I/II assay reagent was prepared by (1) rehydration of lyophilized HDAC-Glo I/II substrate (with an acetylated peptide concentration of 100 µM) in 10 mL HDAC-Glo I/II assay buffer and (2) addition of 10 µL of developer reagent (containing trypsin). The microtiter plates were mixed briefly by orbital shaking (500-700 rpm), and luminescence was measured at steady-state signal: background, which was achieved after 20 min.

SIRT7 Assay

Inhibition of SIRT7 enzyme (in triplicate) was determined using the homogeneous, single-addition, luminescent SIRT-Glo™ assay (Promega Corp.). The assay uses an acetylated, luminogenic peptide substrate that can be deacetylated by SIRT activities. Deacetylation of the peptide aminoluciferin substrate is measured using a coupled enzymatic system in which a protease in the Developer Reagent cleaves the deacetylated peptide from the aminoluciferin substrate, releasing aminoluciferin, which is quantified in a reaction using a proper luciferase. The aminoluciferin product of that cleavage acts as a substrate for luciferase, and the amount of light produced in this reaction is proportional to SIRT enzyme activity. Human recombinant SIRT7 enzyme was purchased from BPS Bioscience (San Diego, CA). Plate handling was performed using an Echo 550 Liquid Handler and luminescence measurements taken using a 2300 EnSpire Multilabel reader. The compounds (final concentration of 10

μM and 0.1% v/v DMSO) and low/high control (final 0.1% v/v DMSO) were added into the 384-well plates (10 nL/well; 0.1% v/v DMSO) using the Echo 550 Liquid Handler. The SIRT-Glo™ assay reagent was prepared by (1) rehydration of lyophilized SIRT substrate (with an acetylated peptide concentration of 100 μM) in 10 mL SIRT-Glo™ assay buffer and (2) addition of 10 μL of developer reagent. The microtiter plates were mixed briefly by orbital shaking (500-700 rpm), and luminescence was measured at steady-state signal: background, which was achieved after 30 min.

PDE Inhibition

The Predictor hERG fluorescence polarization assay (Thermo) was used to test compounds for potential cardiotoxicity (in triplicate). Phosphodiesterases catalyze the hydrolysis of the phosphodiester bond in dye-labeled cyclic monophosphates. Beads selectively bind the phosphate group in the nucleotide product. This increases the size of the nucleotide relative to unreacted cyclic monophosphate. In the polarization assay, dye molecules with absorption transition vectors parallel to the linearly-polarized excitation light are selectively excited. Dyes attached to the rapidly-rotating cyclic monophosphates will obtain random orientations and emit light with low polarization.

Dyes attached to the slowly-rotating nucleotide-bead complexes will not have time to reorient and therefore will emit highly polarized light. To each well of an assay plate, 5 nL of the test/control compound were added followed by addition of 2.5 μL/well of substrate solution (100 nM of final concentration in assay) and 2.5 μL/well of enzyme solution (20 pM of final concentration in assay). The plates were incubated for 1 h protected from light at RT. Then, 10 μL of binding agent were added to each well and plates were incubated at RT for 20 min protected from light. Fluorescence polarization was measured using an EnVision Multilabel 2103 Reader. The NCs (0% inhibition) and positive controls (no enzyme, yielding 100% inhibition), were used to normalize the raw data.

Statistical Analysis

Statistical analyses were performed using GraphPad Prism version 6.0 for Windows (GraphPad Software, San Diego, Calif., USA). Data were subjected to one-way analysis of variance for mean comparison, and significant differences among different treatments were calculated according to Tukey's HSD (honest significant difference) multiple range test. Data are reported as mean±SEM. Differences at $p<0.05$ were considered statistically significant. All the analyses were performed in triplicate.

EXAMPLE 16

Early Compound-Mediated Toxicity and Liability Studies

Figure 5:
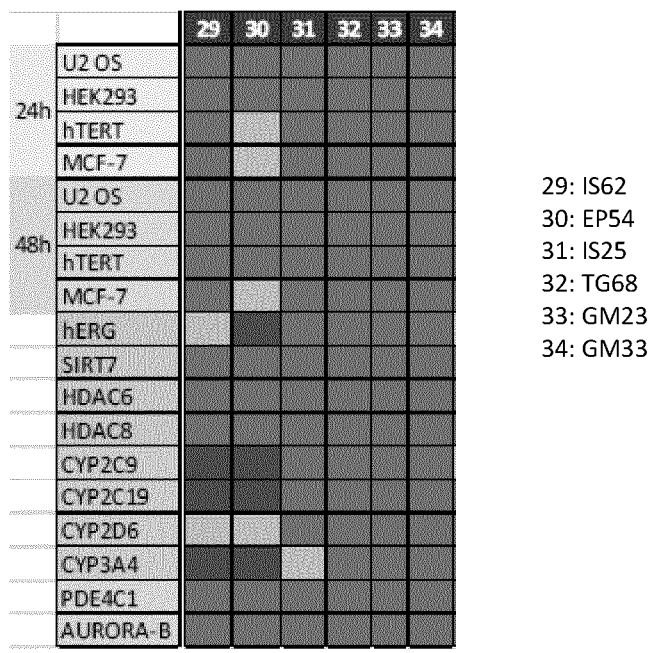
FIG. 5. ADME-TOX profiling In order to assess the ADME-TOX profile of new synthetized compounds a full panel of in vitro assays was performed. Cytotoxic effects were evaluated on 4 different cell lines (U2-OS, HEK293, hTERT, MCF-7) at 24 h and 48 h after treatment with new compounds. Cardiac toxicity was assessed evaluating the inhibition effect of compounds on the hERG ion-channel, an important anti-target involved in heart functionalities. Metabolic interference was evaluated testing inhibitory effects of new compounds on four isoforms of CYP450 (CYP2C9, CYP2C19, CYP2D6, CYP3A4). In order to assess off-target liabilities, the inhibitory effects have been assessed against several well-known off-targets. HDAC6, HDAC8, and SIRT7 were chosen as representatives of an undesirable epigenetic modulation. Moreover, compounds were screened against phosphodiesterase (PDE4C1) and Aurora-B kinase, proteins known for their role in cell survival and tumorogenesis. All screening experiments were performed at a concentration of 10 μM (triplicate) where the results for each compound were normalized using the respective raw data to high and low controls. The data were collected and analyzed in the form of a traffic-light system using criteria shown below.

The new thyromimetics were evaluated using a panel of early-toxicity assays comprising cytotoxicity (U2O5, Human Bone Osteosarcoma Epithelial Cells, HEK 293, Human embryonic kidney cells, MCF-7, human breast adenocarcinoma cell line, hTERT immortalized cell lines), hERG inhibition, cytochrome P450 inhibition (CYP2C9, CYP2C19, CYP2D6, and CYP3A4), off-targets kinases (Aurora B kinase inhibition), PDE inhibition and inhibitory activity on epigenetic modulators (SIRT7, HDAC6 and HDAC8). These experiments were performed using 10 μM of each compound and the output was expressed as % inhibition, which is displayed as a heat map in FIG. 5. An acceptable profile for compounds at this stage in the drug discovery process should exhibit <50% inhibition at 10 μM in the case of hERG, CYP isoforms, and Aurora B kinase, whereas the percentage of viability in cell cytotoxicity should be >50%. Almost all evaluated compounds showed a safe profile. In particular, IS25 and TG68 showed a safer profile (and were then selected for in vivo investigations).

EXAMPLE 17

Evaluation of the Compounds of Formula (I)

The compounds of Formula (I,II) were tested in the biological test named LANTHASCREEN TR-FRET NUCLEAR RECEPTOR COREGULATOR ASSAY (Invitrogen Corporation, Life Technologies).

The compounds synthetized were hence subjected to the LanthaScreen™ TR-FRET Coregulator Assay. In this assay Nuclear Receptor-LBD is added to ligand test compounds followed by addition of a mixture of the fluorescein-coregulator peptide and terbium anti-GST antibody. After an incubation period at room temperature, the TR-FRET ratio of 520:495 is calculated and used to determine the $EC_{50}$ from a dose response curve of the compounds. Based on the biology of the Nuclear receptor-coregulator peptide interaction, this ligand $EC_{50}$ is a composite value representing the amount of ligand required to bind to receptor, effect a conformational change, and recruit coregulator peptide.

As example of the activity the $EC_{50}$ values of IS25 and TG68 are reported.

| Cmpd Name | Nuclear Receptor | EC50 (nM) | $R^2$ Value | Z' |
|---|---|---|---|---|
| IS25 | TR-alpha | >1000 | 0.9876 | 0.92 |
| IS25 | TR-beta | 458 | 0.9962 | 0.86 |
| TG68 | TR-alpha | >1000 | 0.5058 | 0.92 |
| TG68 | TR-beta | >1000 | 0.6828 | 0.86 |
| T3 | TR-alpha | 0.221 | | |
| T3 | TR-beta | 0.220 | | |

In the table have been also reported the data collected in the Lanthascreen TR-FRET nuclear receptor coregulatory assay for thyroid hormone T3. Data collected indicate that IS25 and TG68 do not interact with TRalpha receptor

EXAMPLE 18

Evaluation of the In Vitro Effect of Newly IS25 and TG68 on AMPK Activation

Figure 3:
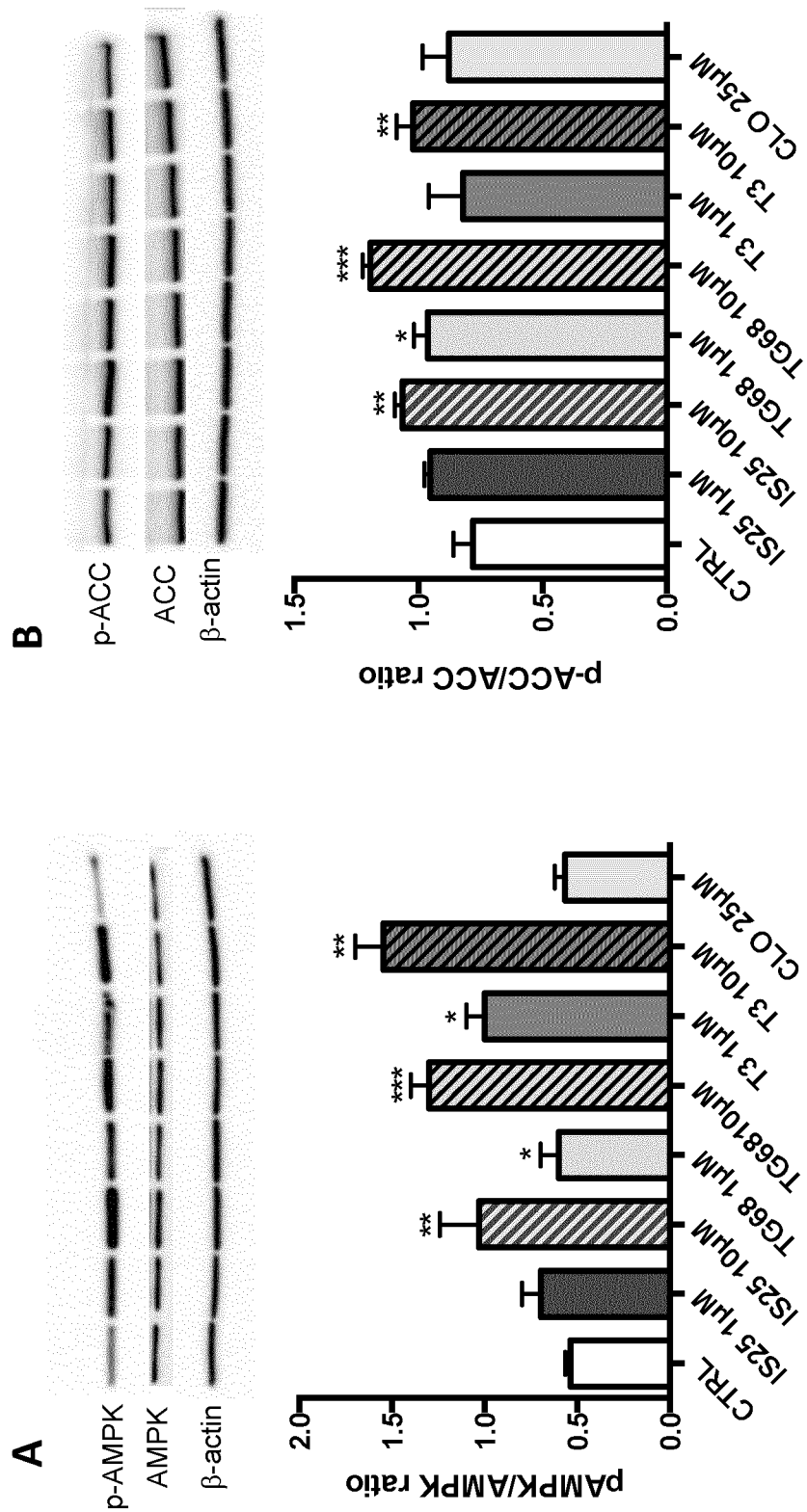
FIG. 3. IS25 and TG68 regulate metabolism in HepG2 cells via AMPK/ACC pathway. A) Representative immunoblotting images and the quantitative analysis of phosphorylation of AMPK. B) Representative immunoblotting images and the quantitative analysis of phosphorylation of ACC. * p<0.05;  p<0.01; * p<0.005

The liver is a major organ responsible for most functions of cellular metabolism and a mediator between dietary and endogenous sources of energy for extrahepatic tissues. In this context, AMPK constitutes an intrahepatic energy sensor regulating physiological energy dynamics by limiting anabolism and stimulating catabolism, thus increasing ATP availability. Once activated, AMPK phosphorylates its downstream substrates to reduce ATP-consuming anabolic pathways, including cholesterol, fatty acid, and triacylglycerol synthesis, and increases ATP-generating catabolic pathways, including fatty acid oxidation and lipolysis. An important downstream target of phosphorylated AMPK (phospho-AMPK) is acetyl-CoA carboxylase (ACC), which catalyzes the production of malonyl-CoA from acetyl-CoA and is one of the initial steps of fatty acid synthesis (14, 15). When ACC activity is high, a greater concentration of malonyl-CoA is produced. Malonyl-CoA binds and inhibits CPT1, thereby reducing the amount of fatty acyl-CoA entering mitochondria, and consequently, FAO. To investigate whether compounds regulate metabolism in HepG2 cells via AMPK pathway, the protein levels of phosphorylated AMPK (p-AMPK), and phosphorylated ACC (p-ACC) were examined. As demonstrated in FIG. 3A, twenty-four hours of treatment with compound IS25, TG68 or T3 significantly ($p<0.05$) increased the expression of p-AMPK in a dose dependent manner. Notably, concomitantly to AMPK stimulation a significant ACC phosphorylation was also observed (FIG. 3B).

EXAMPLE 19

Effects Induced on Lipid Accumulation and Lipolysis

Figure 2:
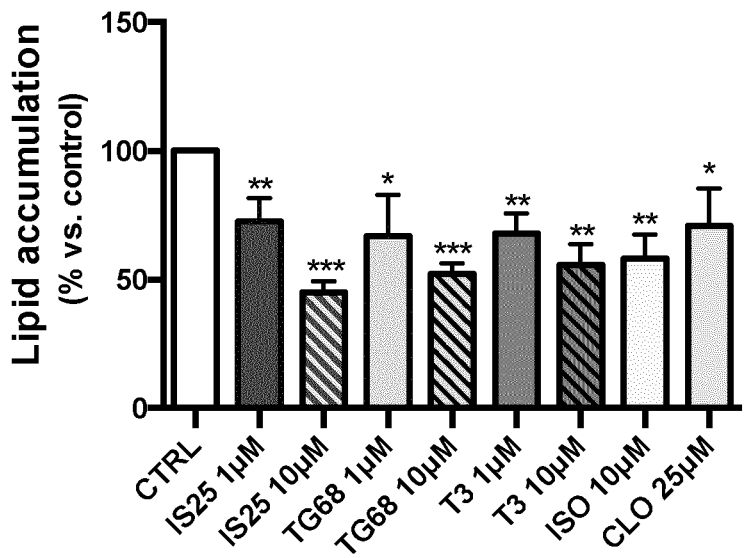
FIG. 2. Effects of IS25 and TG68 on total lipid accumulation in HepG2 cells. Cells were treated for 24 h with IS25, TG68 or T3 at two doses (1-10 μM). 10 μM Isoproterenol (ISO) and 25 μM Cloroquine (CLO) were used as positive controls. Oil red O stained intercellular oil droplets were eluted with isopropanol and quantified by spectrophotometry analysis at 510 nm. Values represent the mean±SEM of 4 to 8 experiments. The groups were compared using the One-Way ANOVA followed by Tukey's range test. * p<0.05;  p<0.01; * p<0.005

Abnormal triglyceride accumulation in the form of lipid droplets can occur in hepatocytes of obese mammals. In vitro, dramatic lipid accumulation can be observed in HepG2 cells treated with steatosis-inducing compounds such as chloroquine. Triglycerides stored in these lipid droplets can be hydrolyzed into free fatty acids and glycerol that are subsequently released into the surrounding environment. The amount of glycerol released into the medium is proportional to the triglyceride/fatty acid cycling rate. The oil red O staining results are displayed in FIG. 2. HepG2 cells treated with 25 µM Cloroquine contain a high amount of red lipid droplets fused to each other, which indicated that the HepG2 cell lipid accumulated model was successfully established. HepG2 red lipid droplets show a significant ($p<0.05$) dose-dependent decreasing trend after treatment with test compounds.

Figure 1:
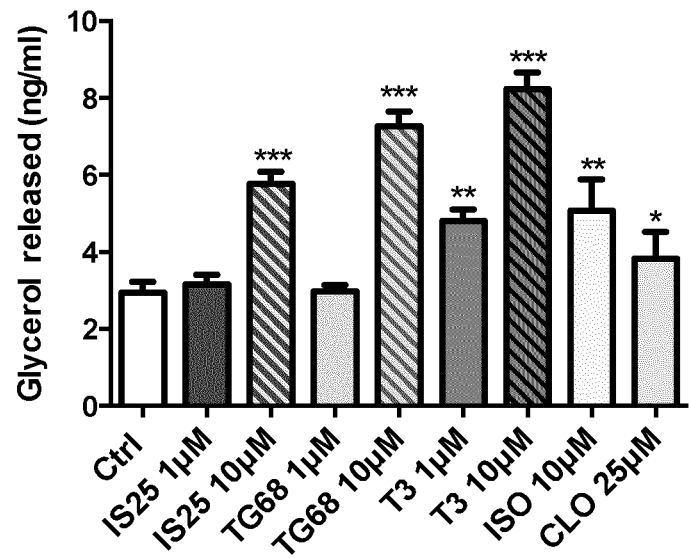
FIG. 1. IS25 and TG68 induce lipolysis in HepG2 cells. Glycerol released in the culture medium (0.5 ml) of HepG2 cells after 24 hours treatment with IS25, TG68 and T3 at two doses (1 and 10 μM). 10 μM Isoproterenol (ISO) and 25 μM Cloroquine (CLO) were used as positive controls. Values represent the mean±SEM of 4 to 8 experiments. The groups were compared using the One-Way ANOVA followed by Tukey's range test. * p<0.05;  p<0.01; * p<0.005

As shown in FIG. 1, incubation with test compounds elicited marked glycerol release by HepG2, in a dose-dependent manner, confirming that newly designed thyromimetic are able to effectively induce lipolysis in HepG2 cells.

EXAMPLE 20

Effects Induced on HepG2 Cell Viability

Figure 4:
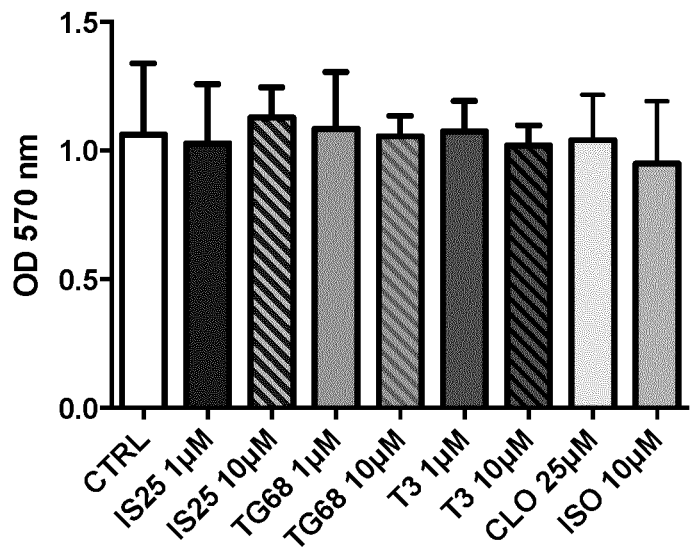
FIG. 4. IS25 and TG68 do not promote toxicity in HepG2 cells. Cell viability after 24 hours of IS25 and TG68 or T3 incubation. Concentrations range from 1 to 10 μM. Cell viability was assessed by MTT assay. Values represent the mean±SEM of three independent experiments.

Viability of HepG2 cells treated with analog IS25, TG68 or T3 at 1-10 µM was determined using the MTT assay. The results showed that after 24 h of treatment all compounds tested did not significantly ($p<0.05$) cause cell death with respect to control (FIG. 4).

EXAMPLE 21

Mitogenic Activity of TG68 and IS25

Five-week-old male F-344 rats purchased from Charles River (Milano, Italy) were maintained on a standard laboratory diet (Ditta Mucedola, Milano, Italy). The animals were given food and water ad libitum with a 12-h light/dark daily cycle and were acclimated for 1 week before the start of the experiment. All procedures were performed in accordance with the Guidelines for the Care and Use of Laboratory Animals and were approved by the Italian Ministry of Health. Animals were treated with daily intragastric (i.g.) injections for 3 days of IS25 or TG68 (50, 75 and 100 µg/100 g b.w) or T3 (20 µg/100 g bw). A control group received the vehicle (DMSO 5% in corn oil). Additional two groups received daily injections of either IS25 or TG68 at the dose of 75 µg/100 g b.wt. intraperitoneally for 3 days. For the measurement of hepatocyte proliferation, animals received bromodeoxyuridine (BrdU; 1 g/1 L) in drinking water during the 3-day treatment period (FIGS. 7A and B).

Effect of T3, IS25 and TG68 on Liver/Body Weight Ratio

F344 male rats were treated for 3 days with daily intragastric (i.g) injections of IS25 or TG68 (50, 75 and 100 µg/100 g b.w.) or T3 (20 µg/100 g b.w.). A control group received the vehicle (DMSO 5% in corn oil). Additional two groups received daily injections of either IS25 or TG68 at the dose of 75 µg/100 g b.w. intraperitoneally for 3 days. At sacrifice, a decreased liver/body weight ratio was observed following T3 treatment, while no such effect was observed with any of the doses of IS25 or TG68 (FIG. 6).

Effect of T3, IS25 and TG68 on Mitotic Activity of Hepatocytes

Since T3 exerts a powerful mitogenic effect in the liver, we investigated whether IS25 and TG68 could also elicit a proliferative response in this organ.

As shown in FIG. 7 intragastric (i.g.) administration of IS25 or TG68 induced a dose dependent hepatocyte proliferation, as assessed by BrdU incorporation. On the contrary when both compounds were administered by i.p. injection the mitogenic effect was lost. Since both compounds resulted to be very soluble in water, they were also submitted to preliminary investigation to evaluate whether two novel TRb or TRβ agonists, could stimulate hepatocyte proliferation.

TG68 and IS25 were dissolved in drinking water at 3 different concentrations (12.5, 25 and 50 µg/100 g b.w.). The highest dose of both the compounds was selected on the basis of the mitogenic activity on rat and mouse liver showed by a similar dose of the analog GC-1 [Endocrinology 2006; 147(7):3211-8, J Hepatol 2010; 53(4):686-92], whereas the oral administration was chosen as the ideal route of administration for future translational studies.

Histologic examination did not show any clear evidence of liver damage in treated animals compared to controls. Lack of severe liver toxicity was confirmed by measuring the levels of serum transaminases and bilirubin (FIG. 8) that were within the range of normal values for F-344 rats of the same age (Charles River datasheet). Pancreas damage was also evaluated by measuring the levels of amylase and lipase. No significant changes were observed for both compounds (FIG. 8). While no change in the content of serum cholesterol and glucose was observed, serum TGs level was significantly reduced after intragastric administration of IS25 or TG68, confirming the lipolytic effect observed by treating HepG2 cells with both compounds.

Effect of Mitogenic Activity of IS25 and TG68 with Respect to GC-1 as Reference Drug The experiment was performed on untreated rats or rats treated with T3, GC1, TG68 or IS25 for one week. T3 was administered in the diet (4 mg/kg diet); GC1 (50 µg/kg) was given by gavage once daily; TG68 and IS25 were dissolved in drinking water at a dose of 50 µg/kg. BrdU (1 mg/ml) in drinking water was given all throughout the experimental time. Several BrdU-positive acinar cells were observed in the pancreas of T3 and GC1-treated rats, but not in TG68 and IS25-treated animals; FIG. 9 shows the LI of rat pancreatic acinar cells. LI was expressed as number of BrdU-positive acinar cell nuclei/100 nuclei. At least 2000 acinar cells per pancreas were scored. Preliminary results hence showed that, unlike T3 or GC-1 (chosen as reference drug), IS25 and TG68 were mitogenic only for the liver and not for other tissues, such as the acinar cell compartment of the pancreas.

REFERENCES CITED

1. Yen P M. Physiological and molecular basis of thyroid hormone action. *Physiological reviews* (2001) 81(3): 1097-142.
2. Kapoor R, Fanibunda S E, Desouza L A, Guha S K, Vaidya V A. Perspectives on thyroid hormone action in adult neurogenesis. *Journal of neurochemistry* (2015) 133(5):599-616.
3. Baxi E G, Schott J T, Fairchild A N, Kirby L A, Karani R, Uapinyoying P, et al. A selective thyroid hormone β receptor agonist enhances human and rodent oligodendrocyte differentiation. *Glia* (2014) 62(9):1513-29. doi: 10.1002/glia.22697. PubMed PMID: PMC4107024.
4. Vaitkus J A, Farrar J S, Celi F S. Thyroid Hormone Mediated Modulation of Energy Expenditure. *International journal of molecular sciences* (2015) 16(7): 16158-75. doi: 10.3390/ijms160716158. PubMed PMID: 26193258.
5. Tancevski I, Eller P, Patsch J R, Ritsch A. The resurgence of thyromimetics as lipid-modifying agents. *Current opinion in investigational drugs* (London, England: 2000) (2009) 10(9):912-8. PubMed PMID: PMC2993058.
6. Gullberg H, Rudling M, Salto C, Forrest D, Angelin B, Vennstrom B. Requirement for thyroid hormone receptor beta in T3 regulation of cholesterol metabolism in mice. *Molecular endocrinology* (Baltimore, Md.) (2002) 16(8):1767-77. Epub 2002/07/30. doi: 10.1210/me.2002-0009. PubMed PMID: 12145333.
7. Kowalik M A, Columbano A, Perra A. Thyroid Hormones, Thyromimetics and Their Metabolites in the Treatment of Liver Disease. *Frontiers in Endocrinology* (2018) 9(382). doi: 10.3389/fendo.2018.00382.
8. Fanti M, Perra A, Pibiri M, Schwartz M, Monga S P, Ledda-Columbano G, et al. Wnt/β-catenin pathway is activated by thyroid hormone and is required for its hepatomitogenic activity. *Federation of American Societies for Experimental Biology* (2012).
9. Singh B K, Sinha R A, Yen P M. Novel Transcriptional Mechanisms for Regulating Metabolism by Thyroid Hormone. *Int J Mol Sci* (2018) 19(10). Epub 2018 Oct. 27. doi: 10.3390/ijms19103284. PubMed PMID: 30360449; PubMed Central PMCID: PMCPmc6214012.
10. Sinha R A, You S H, Zhou J, Siddique M M, Bay B H, Zhu X, et al. Thyroid hormone stimulates hepatic lipid catabolism via activation of autophagy. *J Clin Invest* (2012) 122(7):2428-38. Epub 2012 Jun. 12. doi: 10.1172/jci60580. PubMed PMID: 22684107; PubMed Central PMCID: PMCPmc3386813.
11. Hwang J T, Kwon D Y, Yoon S H. AMP-activated protein kinase: a potential target for the diseases prevention by natural occurring polyphenols. *New biotechnology* (2009) 26(1-2):17-22. Epub 2009 Oct. 13. doi: 10.1016/j.nbt.2009.03.005. PubMed PMID: 19818314.
12. Gasparrini M, Giampieri F, Alvarez Suarez J M, Mazzoni L, T Y F H, Quiles J L, et al. AMPK as a New Attractive Therapeutic Target for Disease Prevention: The Role of Dietary Compounds AMPK and Disease Prevention. *Current drug targets* (2016) 17(8):865-89. Epub 2016 Feb. 5. PubMed PMID: 26844571.
13. Zhang M, Ma Z, Qin H, Yao Z. Thyroid Hormone Potentially Benefits Multiple Sclerosis via Facilitating Remyelination. *Molecular Neurobiology* (2016) 53(7): 4406-16. doi: 10.1007/s12035-015-9375-z.
14. Wakil S J, Abu-Elheiga L A. Fatty acid metabolism: target for metabolic syndrome. *Journal of lipid research* (2009) 50 Suppl:S138-43. Epub 2008 Dec. 3. doi: 10.1194/jlr.R800079-JLR200. PubMed PMID: 19047759; PubMed Central PMCID: PMCPmc2674721.
15. Saggerson D. Malonyl-CoA, a key signaling molecule in mammalian cells. *Annual review of nutrition* (2008) 28:253-72. Epub 2008 Jul. 5. doi: 10.1146/annurev.nutr.28.061807.155434. PubMed PMID: 18598135.

The invention claimed is:

1. A compound of Formula (I) or a salt thereof:

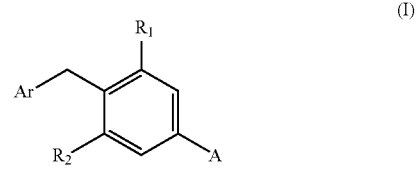

Wherein
$R_1$ is H, $(C_1-C_3)$alkyl or $CF_3$;
$R_2$ is H, $(C_1-C_3)$alkyl or $CF_3$;
A is $CH_2COOH$, $XCH_2COOCH_2CH_3$, $XCH_2COOH$, $XCH_2CH_2NH_2$, where X is nitrogen or oxygen atom;
Ar is an aromatic fragment selected from the group consisting of

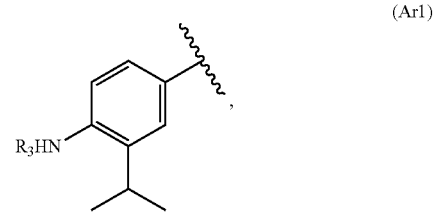

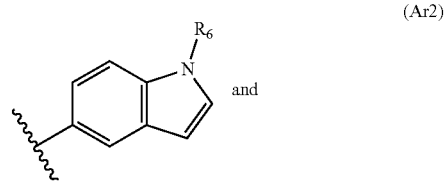

and

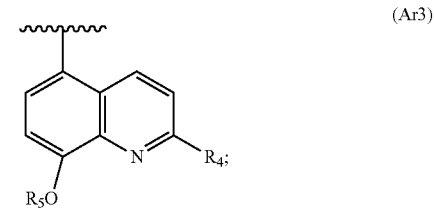

where
$R_3$ is H, —CH$_3$, —CH$_2$CH$_3$ or CH$_3$CO—,
$R_4$ is H or —CH$_3$,
$R_5$ is H or —CH$_3$, and
$R_6$ is H or —CH$_3$.

2. The compound of claim 1 wherein $R_1$ is (C$_1$-C$_3$)alkyl.

3. The compound of claim 1, wherein $R_2$ is (C$_1$-C$_3$)alkyl.

4. The compound of claim 1, wherein A is XCH$_2$COOH.

5. The compound of claim 4, wherein X is oxygen.

6. The compound of claim 1, wherein Ar è Ar1.

7. The compound of claim 6, wherein $R_3$ is CH$_3$CO—.

8. The compound of claim 1, wherein Ar is Ar2 or Ar3.

9. The compound of claim 8, wherein $R_6$ and $R_4$ are independently from each other —CH$_3$.

10. The compound of claim 1, wherein the compound of Formula (I) is selected from the group consisting of:
   2-(4-(4-amino-3-isopropylbenzyl)-3,5-dimethylphenoxy) acetic acid (IS25),
   4-(4-(2-aminoethoxy)-2,6-dimethylbenzyl)-N-ethyl-2-isopropylaniline (IS62),
   2-(4-(4-amino-3-isopropylbenzyl)-3-methylphenoxy)acetic acid (TR29)
   (4-(4-acetamido-3-isopropylbenzyl)-3,5-dimethylphenoxy)acetic acid (TG68),
   4-(4-(2-aminoethoxy)-2-(trifluoromethyl)benzyl)-N-ethyl-2-isopropylaniline hydrochloride (EP54),
   2-(4-(4-amino-3-isopropylbenzyl)-3-(trifluoromethyl)phenoxy)acetic acid (TR30),
   2-(4-(4-acetamido-3-isopropylbenzyl)-3-(trifluoromethyl)phenoxy)acetic acid (TR45),
   2-(4-(4-acetamido-3-isopropylbenzyl)phenoxy)acetic acid (GM23),
   2-(4-(4-amino-3-isopropylbenzyl)phenoxy)acetic acid (GM33),
   2-(4-(4-acetamido-3-isopropylbenzyl)-3-methylphenoxy) acetic acid (GM21),
   (4-(4-acetamido-3-isopropylbenzyl)phenyl)glycine (PA8),
   ethyl (4-(4-acetamido-3-isopropylbenzyl)phenyl)glycinate (PA6),
   N$^1$-(4((8-methoxy-2-methylquinolin-5-yl)methyl)phenyl) ethane-1,2-diamine (GM10), 2-((4-((8-methoxy-2-methylquinolin-5-yl)methyl)phenyl)amino)acetic acid (GM24),
   (4-((1-methyl-1H-indol-5-yl)methyl)phenyl)glycine (TR201), and
   2-(4-(4-acetamido-3-isopropylbenzyl)-3-methylphenyl) acetic acid (RM81).

11. The compound of claim 10, wherein the compound of Formula (I) is selected from the group consisting of 2-(4-(4-acetamido-3-isopropylbenzyl)-3,5-dimethylphenoxy) acetic acid (TG68) and 2-(4-(4-amino-3-isopropylbenzyl)-3,5-dimethylphenoxy)acetic acid (IS25).

12. A pharmacological composition comprising the compound of Formula (I) or a pharmaceutically acceptable salt thereof according to claim 1 and a carrier.

13. A method for the treatment of diseases modulated by thyroid hormone receptor-beta (TRb or TRβ), wherein the diseases modulated by thyroid hormone receptor-beta (TRb or TRβ) are liver diseases, non-alcoholic fatty liver disease (NAFLD), non-alcoholic steatohepatitis (NASH), hepatocellular carcinoma (HCC), dyslipidemia, neurodegenerative diseases, multiple sclerosis, Alzheimer's disease and Parkinson's disease (PD), comprising the step of administering the compound of formula (I) or a pharmaceutically acceptable salt thereof according to claim 1.

14. The compound of claim 1, wherein $R_1$ is methyl.

15. The compound of claim 1, wherein $R_2$ is methyl.

16. The pharmaceutical composition according to claim 12, wherein the compound of Formula (I) or a pharmaceutically salt thereof is a selective modulator of thyroid hormone receptor-beta (TRβ).

* * * * *